(12) United States Patent
MacDonald et al.

(10) Patent No.: US 11,996,189 B2
(45) Date of Patent: May 28, 2024

(54) MANAGEMENT OF PHARMACY KITS

(71) Applicant: Bluesight, Inc., Alexandria, VA (US)

(72) Inventors: Kevin William MacDonald, Washington, DC (US); Timothy James Leo Kress-Spatz, Washington, DC (US)

(73) Assignee: Bluesight, Inc., Alexandria, VA (US)

( * ) Notice: Subject to any disclaimer, the term of this patent is extended or adjusted under 35 U.S.C. 154(b) by 0 days.

(21) Appl. No.: 17/448,310

(22) Filed: Sep. 21, 2021

(65) Prior Publication Data

US 2022/0238219 A1 Jul. 28, 2022

Related U.S. Application Data

(63) Continuation of application No. 15/787,204, filed on Oct. 18, 2017, now Pat. No. 11,139,075, which is a
(Continued)

(51) Int. Cl.
*G16H 40/63* (2018.01)
*G06K 7/10* (2006.01)
(Continued)

(52) U.S. Cl.
CPC ......... *G16H 40/63* (2018.01); *G06K 7/10415* (2013.01); *G06Q 10/087* (2013.01);
(Continued)

(58) Field of Classification Search
CPC ........ G16H 40/63; G16H 15/00; G16H 20/10; G16H 40/40; G16H 40/67; G06K 7/10415;
(Continued)

(56) References Cited

U.S. PATENT DOCUMENTS

| 4,884,827 A | 12/1989 | Kelley |
| 4,961,533 A | 10/1990 | Teller et al. |
| (Continued) | | |

FOREIGN PATENT DOCUMENTS

| CA | 2 722 328 | 10/2009 |
| CA | 2 790 220 | 6/2013 |
| (Continued) | | |

OTHER PUBLICATIONS

Mehrjerdi, Yahia Zare, "RFID-Enabled Healthcare Systems: Risk-Benefit Analysis", International Journal of Pharmaceutical and Healthcare Marketing, 2010, vol. 4, No. 3, pp. 282-300.
(Continued)

*Primary Examiner* — Eliza A Lam
(74) *Attorney, Agent, or Firm* — Knobbe, Martens, Olson & Bear, LLP

(57) ABSTRACT

A system for managing pharmacy kits comprises a reading station configured to read tag information from a plurality of radio frequency identification (RFID) tags associated with a pharmacy kit, and an information processing system operatively connected to the reading station and configured to receive the tag information from the reading station and determine a status of the pharmacy kit based on the tag information, a plurality of stored templates defining contents to be included in each of a plurality of pharmacy kits, and a plurality of kit records indicating the current contents of a plurality of pharmacy kits.

37 Claims, 22 Drawing Sheets

Related U.S. Application Data continuation of application No. 14/701,958, filed on May 1, 2015, now Pat. No. 9,805,169, which is a continuation of application No. 14/603,730, filed on Jan. 23, 2015, now Pat. No. 9,058,412, which is a continuation of application No. 13/554,342, filed on Jul. 20, 2012, now Pat. No. 8,990,099.

(60) Provisional application No. 61/514,231, filed on Aug. 2, 2011.

(51) Int. Cl.
*G06Q 10/087* (2023.01)
*G06Q 10/0875* (2023.01)
*G06Q 10/10* (2023.01)
*G16H 15/00* (2018.01)
*G16H 20/10* (2018.01)
*G16H 40/40* (2018.01)
*G16H 40/67* (2018.01)
*G16Z 99/00* (2019.01)
*H04W 4/80* (2018.01)

(52) U.S. Cl.
CPC ......... *G06Q 10/0875* (2013.01); *G06Q 10/10* (2013.01); *G16H 15/00* (2018.01); *G16H 20/10* (2018.01); *G16H 40/40* (2018.01); *G16H 40/67* (2018.01); *G16Z 99/00* (2019.02); *H04W 4/80* (2018.02)

(58) Field of Classification Search
CPC .. G06Q 10/087; G06Q 10/0875; G06Q 10/10; G16Z 99/00; H04W 4/80
See application file for complete search history.

(56) References Cited

U.S. PATENT DOCUMENTS

| | | |
|---|---|---|
| 5,713,485 A | 2/1998 | Liff et al. |
| 5,930,145 A | 7/1999 | Yuyama et al. |
| 5,963,134 A | 10/1999 | Bowers et al. |
| 5,986,662 A | 11/1999 | Argiro et al. |
| 6,112,502 A | 9/2000 | Frederick et al. |
| 6,249,299 B1 | 6/2001 | Tainer |
| 6,275,157 B1 | 8/2001 | Mays et al. |
| 6,294,999 B1 | 9/2001 | Yarin et al. |
| 6,330,351 B1 | 12/2001 | Yasunaga |
| 6,574,166 B2 | 6/2003 | Niemiec |
| 6,632,619 B1 | 10/2003 | Harrison et al. |
| 6,771,369 B2 | 8/2004 | Rzasa et al. |
| 6,825,864 B2 | 11/2004 | Botten et al. |
| 6,847,861 B2 | 1/2005 | Lunak et al. |
| 6,851,615 B2 | 2/2005 | Jones |
| 6,861,954 B2 | 3/2005 | Levin |
| 6,877,658 B2 | 4/2005 | Raistrick et al. |
| 6,879,876 B2 | 4/2005 | O'Dougherty et al. |
| 6,900,021 B1 | 5/2005 | Harrison et al. |
| 6,933,849 B2 | 8/2005 | Sawyer |
| 6,935,560 B2 | 8/2005 | Andreasson et al. |
| 6,952,681 B2 | 10/2005 | McQuade et al. |
| 6,985,870 B2 | 1/2006 | Martucci et al. |
| 6,992,574 B2 | 1/2006 | Aupperle et al. |
| 6,994,249 B2 | 2/2006 | Peterka et al. |
| 7,036,729 B2 | 5/2006 | Chung |
| 7,061,831 B2 | 6/2006 | De La Huerga |
| 7,111,780 B2 | 9/2006 | Broussard et al. |
| 7,116,343 B2 | 10/2006 | Botten et al. |
| 7,118,029 B2 | 10/2006 | Nycz et al. |
| 7,140,542 B2 | 11/2006 | Andreasson et al. |
| 7,146,247 B2 | 12/2006 | Kirsch et al. |
| 7,151,456 B2 | 12/2006 | Godfrey |
| 7,158,030 B2 | 1/2007 | Chung |
| 7,165,077 B2 | 1/2007 | Kalies |
| 7,175,081 B2 | 2/2007 | Andreasson et al. |
| 7,177,721 B2 | 2/2007 | Kirsch et al. |
| 7,178,729 B2 | 2/2007 | Shaffer et al. |
| 7,182,256 B2 | 2/2007 | Andreasson et al. |
| 7,212,100 B2 | 5/2007 | Terenna |
| 7,212,127 B2 | 5/2007 | Jacober et al. |
| 7,227,469 B2 | 6/2007 | Varner et al. |
| 7,232,066 B2 | 6/2007 | Andreasson et al. |
| 7,253,736 B2 | 8/2007 | Tethrake et al. |
| 7,256,699 B2 | 8/2007 | Tethrake et al. |
| 7,263,501 B2 | 8/2007 | Tirinato et al. |
| 7,264,323 B2 | 9/2007 | Tainer et al. |
| 7,268,684 B2 | 9/2007 | Tethrake et al. |
| 7,275,645 B2 | 10/2007 | Mallett et al. |
| 7,299,981 B2 | 11/2007 | Hickle et al. |
| 7,316,231 B2 | 1/2008 | Hickle |
| 7,317,393 B2 | 1/2008 | Maloney |
| 7,318,529 B2 | 1/2008 | Mallett et al. |
| 7,339,550 B2 | 3/2008 | Hayama et al. |
| 7,341,147 B2 | 3/2008 | Mallett et al. |
| 7,348,884 B2 | 3/2008 | Higham |
| 7,354,884 B2 | 4/2008 | Hada et al. |
| 7,362,228 B2 | 4/2008 | Nycz et al. |
| 7,375,737 B2 | 5/2008 | Botten et al. |
| 7,394,383 B2 | 7/2008 | Hager et al. |
| 7,440,818 B2 | 10/2008 | Handfield et al. |
| 7,446,747 B2 | 11/2008 | Youngblood et al. |
| 7,454,880 B1 | 11/2008 | Austin et al. |
| 7,486,188 B2 | 2/2009 | Van Alstyne |
| 7,492,257 B2 | 2/2009 | Tethrake et al. |
| 7,492,261 B2 | 2/2009 | Cambre et al. |
| 7,504,954 B2 | 3/2009 | Spaeder |
| 7,518,502 B2 | 4/2009 | Austin et al. |
| 7,518,516 B2 | 4/2009 | Azevedo et al. |
| 7,551,089 B2 | 6/2009 | Sawyer |
| 7,559,483 B2 | 7/2009 | Hickle et al. |
| 7,564,364 B2 | 7/2009 | Zweig |
| 7,630,791 B2 | 12/2009 | Nguyen et al. |
| 7,639,136 B1 | 12/2009 | Wass et al. |
| 7,644,016 B2 | 1/2010 | Nycz et al. |
| 7,672,872 B2 | 3/2010 | Shanton |
| 7,706,915 B2 | 4/2010 | Mohapatra et al. |
| 7,706,916 B2 | 4/2010 | Hilton |
| 7,712,670 B2 | 5/2010 | Sauerwein, Jr. et al. |
| 7,715,277 B2 | 5/2010 | de la Huerga |
| 7,729,597 B2 | 6/2010 | Wright et al. |
| 7,734,157 B2 | 6/2010 | Wright et al. |
| 7,737,858 B2 | 6/2010 | Matityaho |
| 7,747,477 B1 | 6/2010 | Louie et al. |
| 7,752,085 B2 | 7/2010 | Monroe |
| 7,772,964 B2 | 8/2010 | Tethrake et al. |
| 7,775,056 B2 | 8/2010 | Lowenstein |
| 7,783,163 B2 | 8/2010 | Wright et al. |
| 7,783,174 B2 | 8/2010 | Wright et al. |
| 7,801,422 B2 | 9/2010 | Wright et al. |
| 7,815,117 B2 | 10/2010 | Tuschel et al. |
| 7,834,765 B2 | 11/2010 | Sawyer |
| 7,834,766 B2 | 11/2010 | Sawyer |
| 7,837,093 B1 | 11/2010 | Leu et al. |
| 7,837,107 B1 | 11/2010 | Leu et al. |
| 7,858,841 B2 | 12/2010 | Krautkramer et al. |
| 7,860,730 B1 | 12/2010 | Goodall et al. |
| 7,868,754 B2 | 1/2011 | Salvat, Jr. |
| 7,893,876 B2 | 2/2011 | Brown et al. |
| 7,908,030 B2 | 3/2011 | Handfield et al. |
| 7,918,830 B2 | 4/2011 | Langan et al. |
| 7,928,844 B2 | 4/2011 | Mackenzie et al. |
| 7,933,033 B2 | 4/2011 | Ohishi et al. |
| 7,976,508 B2 | 7/2011 | Hoag |
| 7,985,711 B2 | 7/2011 | Tohmatsu et al. |
| 7,990,272 B2 | 8/2011 | Wass et al. |
| 7,996,286 B2 | 8/2011 | Kreiner et al. |
| 8,002,174 B2 | 8/2011 | Coyne, III et al. |
| 8,006,903 B2 | 8/2011 | Braun et al. |
| 8,009,913 B2 | 8/2011 | Greyshock |
| 8,019,471 B2 | 9/2011 | Bogash et al. |
| 8,031,347 B2 | 10/2011 | Edwards et al. |
| 8,042,738 B2 | 10/2011 | Cloix |
| 8,049,627 B1 | 11/2011 | Addante |
| 8,063,925 B2 | 11/2011 | Tainer et al. |

(56) References Cited

U.S. PATENT DOCUMENTS

| | | |
|---|---|---|
| 8,065,858 B2 | 11/2011 | Leu et al. |
| 8,072,635 B2 | 12/2011 | Roberts et al. |
| 8,077,041 B2 | 12/2011 | Stern et al. |
| 8,082,192 B2 | 12/2011 | Nycz et al. |
| 8,099,339 B1 | 1/2012 | Pinsonneault et al. |
| 8,108,068 B1 | 1/2012 | Boucher et al. |
| 8,111,159 B2 | 2/2012 | Andreasson et al. |
| 8,112,175 B2 | 2/2012 | Handfield et al. |
| 8,131,397 B2 | 3/2012 | Vahlberg et al. |
| 8,154,390 B2 | 4/2012 | Heath et al. |
| 8,174,392 B1 | 5/2012 | Sagbhini et al. |
| 8,186,587 B2 | 5/2012 | Zmood et al. |
| 8,212,677 B2 | 7/2012 | Ferguson |
| 8,219,413 B2 | 7/2012 | Martinez et al. |
| 8,224,483 B1 | 7/2012 | Ansari et al. |
| 8,231,749 B2 | 7/2012 | Dent et al. |
| 8,258,961 B2 | 9/2012 | Phillips et al. |
| 8,261,939 B2 | 9/2012 | Knoth |
| 8,271,128 B1 | 9/2012 | Schultz |
| 8,279,069 B2 | 10/2012 | Sawyer |
| 8,283,287 B2 | 10/2012 | Aihara et al. |
| 8,284,059 B2 | 10/2012 | Ross |
| 8,285,083 B2 | 10/2012 | Canessa et al. |
| 8,285,607 B2 | 10/2012 | Danilewitz |
| 8,286,222 B2 | 10/2012 | Silverbrook et al. |
| 8,292,173 B2 | 10/2012 | Yturralde et al. |
| 8,292,186 B2 | 10/2012 | Deloche et al. |
| 8,296,950 B2 | 10/2012 | Colbrunn et al. |
| 8,313,024 B2 | 11/2012 | Marino |
| 8,319,607 B2 | 11/2012 | Grimlund et al. |
| 8,328,082 B1 | 12/2012 | Bochenko et al. |
| 8,339,649 B2 | 12/2012 | Ohishi et al. |
| 8,341,041 B2 | 12/2012 | Hull |
| 8,346,632 B2 | 1/2013 | Saghbini |
| 8,355,753 B2 | 1/2013 | Bochenko et al. |
| 8,355,962 B2 | 1/2013 | Delaney et al. |
| 8,359,338 B2 | 1/2013 | Butterfield et al. |
| 8,371,448 B1 | 2/2013 | Reaux |
| 8,376,228 B2 | 2/2013 | DeVet et al. |
| 8,384,545 B2 | 2/2013 | Hussain et al. |
| 8,385,972 B2 | 2/2013 | Bochenko et al. |
| 8,386,070 B2 | 2/2013 | Eliuk et al. |
| 8,394,053 B2 | 3/2013 | Bochenko et al. |
| 8,403,212 B2 | 3/2013 | van Esch |
| 8,403,224 B2 | 3/2013 | Fedorko et al. |
| 8,405,508 B2 | 3/2013 | Burke |
| 8,438,067 B2 | 5/2013 | Omura et al. |
| 8,461,076 B2 | 6/2013 | Okada et al. |
| 8,483,550 B2 | 7/2013 | Wright et al. |
| 8,509,604 B2 | 8/2013 | Wright et al. |
| 8,515,251 B2 | 8/2013 | Wright et al. |
| 8,519,849 B2 | 8/2013 | Ross-Messemer |
| 8,530,379 B2 | 9/2013 | Shimizu et al. |
| 8,564,416 B2 | 10/2013 | Steven et al. |
| 8,565,552 B2 | 10/2013 | Sommer et al. |
| 8,582,171 B2 | 11/2013 | Srnka et al. |
| 8,589,271 B2 | 11/2013 | Evans |
| 8,593,278 B2 | 11/2013 | Churbock et al. |
| 8,593,678 B2 | 11/2013 | Ohishi et al. |
| D694,817 S | 12/2013 | Adam et al. |
| 8,600,548 B2 | 12/2013 | Bossi et al. |
| 8,606,596 B1 | 12/2013 | Bochenko et al. |
| 8,636,202 B2 | 1/2014 | Keefe et al. |
| 8,639,525 B2 | 1/2014 | Levine et al. |
| 8,686,859 B2 | 4/2014 | Hussain et al. |
| 8,699,054 B2 | 4/2014 | Edwards et al. |
| 8,702,674 B2 | 4/2014 | Bochenko |
| 8,723,674 B2 | 5/2014 | Conley et al. |
| 8,749,356 B2 | 6/2014 | Hussain et al. |
| 8,755,056 B2 | 6/2014 | Edwards et al. |
| 8,825,680 B2 | 9/2014 | Burke et al. |
| 8,838,215 B2 | 9/2014 | John et al. |
| 8,868,616 B1 | 10/2014 | Otto et al. |
| 8,893,970 B2 | 11/2014 | Keefe et al. |
| 8,922,435 B2 | 12/2014 | Fontecchio et al. |
| 8,935,280 B2 | 1/2015 | Bauman et al. |
| 8,945,066 B2 | 2/2015 | Bochenko et al. |
| 8,948,478 B2 | 2/2015 | Keefe et al. |
| 8,985,388 B2 | 3/2015 | Ratnakar |
| 8,990,099 B2 | 3/2015 | MacDonald et al. |
| 9,037,479 B1 | 5/2015 | MacDonald et al. |
| 9,058,412 B2 | 6/2015 | MacDonald et al. |
| 9,058,413 B2 | 6/2015 | MacDonald et al. |
| 9,058,435 B2 | 6/2015 | Keefe et al. |
| 9,171,280 B2 | 10/2015 | Gitchell et al. |
| 9,189,769 B2 | 11/2015 | Caputo et al. |
| 9,367,665 B2 | 6/2016 | MacDonald et al. |
| 9,449,296 B2 | 9/2016 | MacDonald et al. |
| 9,539,374 B2 | 1/2017 | Halpern |
| 9,582,644 B2 | 2/2017 | Gitchell et al. |
| 9,734,294 B2 | 8/2017 | MacDonald et al. |
| 9,805,169 B2 | 10/2017 | MacDonald et al. |
| 10,083,766 B2 | 9/2018 | Gitchell et al. |
| 10,210,954 B2 | 2/2019 | Caputo et al. |
| 10,600,513 B2 | 3/2020 | Gitchell et al. |
| 10,609,845 B2 | 3/2020 | Elizondo |
| 10,621,394 B2 | 4/2020 | Hussain et al. |
| 10,643,743 B2 | 5/2020 | Caputo et al. |
| 10,658,077 B2 | 5/2020 | Hussain et al. |
| 10,658,078 B2 | 5/2020 | Caputo et al. |
| 10,664,740 B2 | 5/2020 | Elizondo |
| 10,853,380 B1 | 12/2020 | Agnew et al. |
| 10,930,393 B2 | 2/2021 | Gitchell et al. |
| 11,017,352 B2 | 5/2021 | MacDonald et al. |
| 11,037,342 B1 | 6/2021 | Agnew et al. |
| 11,139,075 B2 | 10/2021 | MacDonald et al. |
| 11,551,797 B2 | 1/2023 | Kress-Spatz et al. |
| 11,557,393 B2 | 1/2023 | Gitchell et al. |
| 11,664,105 B2 | 5/2023 | Yanowitz et al. |
| 2002/0026330 A1 | 2/2002 | Klein |
| 2002/0049650 A1 | 4/2002 | Reff |
| 2002/0087360 A1 | 7/2002 | Pettit |
| 2002/0087362 A1 | 7/2002 | Cobb et al. |
| 2002/0087554 A1 | 7/2002 | Seelinger |
| 2003/0055685 A1 | 3/2003 | Cobb et al. |
| 2003/0074223 A1 | 4/2003 | Hickle et al. |
| 2003/0102970 A1 | 6/2003 | Creel et al. |
| 2003/0160698 A1 | 8/2003 | Andreasson et al. |
| 2003/0216974 A1 | 11/2003 | Browne |
| 2004/0008123 A1 | 1/2004 | Carrender et al. |
| 2004/0032330 A1 | 2/2004 | Hoffman |
| 2004/0051368 A1 | 3/2004 | Caputo et al. |
| 2004/0057609 A1 | 3/2004 | Weinberg |
| 2004/0081669 A1 | 4/2004 | Greeven et al. |
| 2004/0158507 A1 | 8/2004 | Meek et al. |
| 2004/0178071 A1 | 9/2004 | Harrison et al. |
| 2004/0215486 A1 | 10/2004 | Braverman |
| 2004/0225528 A1 | 11/2004 | Brock |
| 2005/0014849 A1 | 1/2005 | Pettit et al. |
| 2005/0060171 A1 | 3/2005 | Molnar |
| 2005/0062603 A1 | 3/2005 | Fuerst et al. |
| 2005/0108044 A1 | 5/2005 | Koster |
| 2005/0125097 A1 | 6/2005 | Chudy et al. |
| 2005/0127176 A1 | 6/2005 | Dickinson |
| 2005/0149378 A1 | 7/2005 | Cyr et al. |
| 2005/0149414 A1 | 7/2005 | Schrodt et al. |
| 2005/0184151 A1 | 8/2005 | DiMaggio et al. |
| 2005/0283259 A1 | 12/2005 | Wolpow |
| 2005/0285732 A1 | 12/2005 | Sengupta et al. |
| 2005/0285746 A1 | 12/2005 | Sengupta et al. |
| 2006/0006999 A1 | 1/2006 | Walczyk et al. |
| 2006/0043177 A1 | 3/2006 | Nycz et al. |
| 2006/0043179 A1 | 3/2006 | Nycz et al. |
| 2006/0065726 A1 | 3/2006 | Andreasson et al. |
| 2006/0109105 A1 | 5/2006 | Varner et al. |
| 2006/0132311 A1 | 6/2006 | Kruest et al. |
| 2006/0145871 A1 | 7/2006 | Donati et al. |
| 2006/0152338 A1 | 7/2006 | Hsu |
| 2006/0152364 A1 | 7/2006 | Walton |
| 2006/0152367 A1 | 7/2006 | Narayanaswamy |
| 2006/0208886 A1 | 9/2006 | Beamer |
| 2006/0244593 A1* | 11/2006 | Nycz .............. A61B 90/98 340/572.1 |
| 2006/0267731 A1 | 11/2006 | Chen |

(56) References Cited

U.S. PATENT DOCUMENTS

| | | |
|---|---|---|
| 2007/0001809 A1 | 1/2007 | Kodukula et al. |
| 2007/0008399 A1 | 1/2007 | Botten et al. |
| 2007/0023512 A1* | 2/2007 | Miller .................. G06Q 10/087 235/385 |
| 2007/0023513 A1 | 2/2007 | Andreasson et al. |
| 2007/0074722 A1 | 4/2007 | Giroux et al. |
| 2007/0114279 A1 | 5/2007 | Lessing et al. |
| 2007/0150382 A1 | 6/2007 | Danilewitz |
| 2007/0187475 A1 | 8/2007 | MacLeod |
| 2007/0188306 A1 | 8/2007 | Tethrake et al. |
| 2007/0200702 A1 | 8/2007 | Chung |
| 2007/0213659 A1 | 9/2007 | Trovato et al. |
| 2007/0213684 A1 | 9/2007 | Hickle et al. |
| 2007/0229268 A1* | 10/2007 | Swan ...................... G08B 21/24 340/572.1 |
| 2007/0272746 A1 | 11/2007 | Ortiz et al. |
| 2008/0004908 A1 | 1/2008 | Oh et al. |
| 2008/0012687 A1 | 1/2008 | Rubinstein |
| 2008/0045930 A1 | 2/2008 | Makin et al. |
| 2008/0046295 A1 | 2/2008 | Albrecht |
| 2008/0061153 A1* | 3/2008 | Hickle ................ A61M 16/183 235/492 |
| 2008/0094214 A1 | 4/2008 | Azevedo et al. |
| 2008/0122878 A1 | 5/2008 | Keefe et al. |
| 2008/0128482 A1 | 6/2008 | Chen et al. |
| 2008/0129496 A1 | 6/2008 | Koblasz |
| 2008/0150722 A1 | 6/2008 | Jackson |
| 2008/0157967 A1 | 7/2008 | Jones et al. |
| 2008/0172253 A1 | 7/2008 | Chung et al. |
| 2008/0184719 A1 | 8/2008 | Lowenstein |
| 2008/0186180 A1* | 8/2008 | Butler .................... H04L 67/12 340/572.1 |
| 2008/0191013 A1 | 8/2008 | Liberatore |
| 2008/0218307 A1 | 9/2008 | Schoettle |
| 2008/0228160 A1 | 9/2008 | Harrison |
| 2008/0231456 A1 | 9/2008 | Matityaho |
| 2008/0243088 A1 | 10/2008 | Evans |
| 2008/0270178 A1 | 10/2008 | McRae et al. |
| 2008/0296373 A1 | 12/2008 | Smood et al. |
| 2008/0297356 A1 | 12/2008 | Oberle |
| 2008/0306772 A1 | 12/2008 | Shahrokh |
| 2008/0316045 A1 | 12/2008 | Sriharto et al. |
| 2009/0002173 A1 | 1/2009 | Bergsten et al. |
| 2009/0020442 A1 | 1/2009 | Dietrich et al. |
| 2009/0058653 A1 | 3/2009 | Geissler et al. |
| 2009/0144087 A1 | 6/2009 | Kelsch et al. |
| 2009/0153290 A1 | 6/2009 | Bierach |
| 2009/0164042 A1 | 6/2009 | Handfield et al. |
| 2009/0194987 A1 | 8/2009 | Christie et al. |
| 2009/0224891 A1 | 9/2009 | Vishik et al. |
| 2009/0231138 A1 | 9/2009 | Cheung et al. |
| 2009/0267740 A1 | 10/2009 | Pizzuto et al. |
| 2009/0267772 A1 | 10/2009 | Dehnadi |
| 2009/0277815 A1 | 11/2009 | Kohl |
| 2009/0294521 A1 | 12/2009 | De La Huerga |
| 2010/0022953 A1 | 1/2010 | Bochenko et al. |
| 2010/0022987 A1 | 1/2010 | Bochenko |
| 2010/0036310 A1 | 2/2010 | Hillman |
| 2010/0036678 A1 | 2/2010 | Bray |
| 2010/0036755 A1 | 2/2010 | Saghbini |
| 2010/0042439 A1 | 2/2010 | Martinez et al. |
| 2010/0079337 A1 | 4/2010 | Hsu et al. |
| 2010/0098425 A1 | 4/2010 | Kewitsch |
| 2010/0108761 A1 | 5/2010 | Nycz et al. |
| 2010/0114951 A1 | 5/2010 | Bauman et al. |
| 2010/0185458 A1 | 7/2010 | Calderwood et al. |
| 2010/0204659 A1 | 8/2010 | Bochenko |
| 2010/0217621 A1 | 8/2010 | Schoenberg et al. |
| 2010/0219097 A1 | 9/2010 | Ramasubramanian et al. |
| 2010/0238039 A1 | 9/2010 | Tethrake et al. |
| 2010/0268548 A1 | 10/2010 | Garrett et al. |
| 2010/0275625 A1 | 11/2010 | Lowenstein |
| 2010/0299158 A1 | 11/2010 | Siegel |
| 2010/0328474 A1 | 12/2010 | Hsieh |
| 2010/0332246 A1 | 12/2010 | Fedorko et al. |
| 2011/0006879 A1 | 1/2011 | Bartos |
| 2011/0060455 A1 | 3/2011 | Bogash et al. |
| 2011/0063091 A1 | 3/2011 | Kang |
| 2011/0068922 A1 | 3/2011 | Ross |
| 2011/0112682 A1 | 5/2011 | Matsukawa et al. |
| 2011/0115612 A1 | 5/2011 | Kulinets et al. |
| 2011/0125315 A1 | 5/2011 | Handfield et al. |
| 2011/0131056 A1 | 6/2011 | Chudy et al. |
| 2011/0139871 A1 | 6/2011 | Yturralde et al. |
| 2011/0161112 A1 | 6/2011 | Keefe et al. |
| 2011/0163871 A1 | 7/2011 | Einav et al. |
| 2011/0166878 A1 | 7/2011 | Louie et al. |
| 2011/0184751 A1 | 7/2011 | Holmes |
| 2011/0187549 A1 | 8/2011 | Balasing |
| 2011/0202174 A1 | 8/2011 | Bogash et al. |
| 2011/0225100 A1 | 9/2011 | Sangal et al. |
| 2011/0227722 A1 | 9/2011 | Salvat, Jr. |
| 2011/0240729 A1 | 10/2011 | Schuck |
| 2011/0257991 A1 | 10/2011 | Shukla |
| 2011/0270441 A1 | 11/2011 | Handfield et al. |
| 2011/0291809 A1 | 12/2011 | Niemiec et al. |
| 2011/0301446 A1 | 12/2011 | Kamen |
| 2011/0313395 A1 | 12/2011 | Krulevitch et al. |
| 2012/0037266 A1 | 2/2012 | Bochenko |
| 2012/0041778 A1 | 2/2012 | Kraft |
| 2012/0044054 A1 | 2/2012 | Hussain et al. |
| 2012/0061463 A1 | 3/2012 | Burke |
| 2012/0089411 A1 | 4/2012 | Srnka et al. |
| 2012/0089418 A1 | 4/2012 | Kamath et al. |
| 2012/0116798 A1 | 5/2012 | Heath et al. |
| 2012/0125994 A1 | 5/2012 | Heath et al. |
| 2012/0130534 A1 | 5/2012 | Wurm |
| 2012/0173440 A1 | 7/2012 | Becker et al. |
| 2012/0177256 A1 | 7/2012 | Keefe et al. |
| 2012/0179132 A1 | 7/2012 | Valk et al. |
| 2012/0185951 A1 | 7/2012 | Bauman et al. |
| 2012/0209619 A1 | 8/2012 | Knotts et al. |
| 2012/0240067 A1 | 9/2012 | Bauman et al. |
| 2012/0273087 A1 | 11/2012 | Einy et al. |
| 2012/0278096 A1 | 11/2012 | Holness |
| 2012/0278228 A1 | 11/2012 | Rubinstein |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0038452 A1 | 2/2013 | Sawyer |
| 2013/0041784 A1 | 2/2013 | Danilewitz |
| 2013/0092727 A1 | 4/2013 | Edwards et al. |
| 2013/0105568 A1 | 5/2013 | Jablonski et al. |
| 2013/0151005 A1 | 6/2013 | Gerold et al. |
| 2013/0191149 A1 | 7/2013 | Kolberg et al. |
| 2013/0221082 A1 | 8/2013 | Botten |
| 2013/0221087 A1 | 8/2013 | Keefe et al. |
| 2013/0225945 A1 | 8/2013 | Prince et al. |
| 2013/0327822 A1 | 12/2013 | Keefe et al. |
| 2014/0060729 A1 | 3/2014 | Srnka et al. |
| 2014/0066880 A1 | 3/2014 | Prince et al. |
| 2014/0114472 A1 | 4/2014 | Bossi et al. |
| 2014/0117081 A1 | 5/2014 | Jablonski et al. |
| 2014/0136229 A1 | 5/2014 | Levine et al. |
| 2014/0142975 A1 | 5/2014 | Keefe et al. |
| 2014/0184390 A1 | 7/2014 | Elizondo |
| 2014/0184391 A1 | 7/2014 | Elizondo |
| 2014/0197954 A1 | 7/2014 | Caputo et al. |
| 2014/0210596 A1 | 7/2014 | Hussain et al. |
| 2014/0262919 A1 | 9/2014 | Hussain et al. |
| 2014/0263614 A1 | 9/2014 | Keefe et al. |
| 2014/0276213 A1 | 9/2014 | Bochenko |
| 2014/0282197 A1 | 9/2014 | Keefe et al. |
| 2014/0291397 A1 | 10/2014 | Caputo et al. |
| 2014/0367080 A1 | 12/2014 | Hussain et al. |
| 2015/0058182 A1 | 2/2015 | Kress-Spatz et al. |
| 2017/0132734 A1 | 5/2017 | MacDonald et al. |
| 2017/0212993 A1 | 7/2017 | Gitchell et al. |
| 2019/0088354 A1 | 3/2019 | Yanowitz et al. |
| 2019/0272396 A1 | 9/2019 | Clouser et al. |
| 2020/0013494 A1 | 1/2020 | Caputo et al. |
| 2020/0167534 A1 | 5/2020 | Elizondo |

(56) References Cited

U.S. PATENT DOCUMENTS

| | | | |
|---|---|---|---|
| 2021/0043291 | A1 | 2/2021 | James et al. |
| 2021/0383323 | A1 | 12/2021 | MacDonald et al. |
| 2022/0282199 | A1 | 9/2022 | Vann |

FOREIGN PATENT DOCUMENTS

| | | |
|---|---|---|
| CN | 102791310 B | 12/2014 |
| IN | 2012/04914 P4 | 10/2013 |
| WO | WO 02/095675 | 11/2002 |
| WO | WO 2006/026246 | 3/2006 |
| WO | WO 2006/135830 | 12/2006 |
| WO | WO 2010/074781 | 7/2010 |
| WO | WO 2011/115676 | 9/2011 |
| WO | WO 2011/150013 | 12/2011 |
| WO | WO 2013/082423 | 6/2013 |
| WO | WO 2013/116873 | 8/2013 |
| WO | WO 2013/134256 | 9/2013 |
| WO | WO 2014/159928 | 10/2014 |
| WO | WO 2014/189834 | 11/2014 |

OTHER PUBLICATIONS

Saygin, C., "Adaptive Inventory Management Using RFID Data", The International Journal of Advanced Manufacturing Technology, 2007, vol. 32, pp. 1045-1051.

Singh et al., "Versatility of Radio Frequency Identification (RFID) Tags in the Pharmaceutical Industry", Instrumentation Science and Technology, vol. 36, pp. 656-663, 2008.

Exhibit B; Deposition of Jeffrey Fischer, *Health Care Logistics, Inc. v. Kit Check, Inc.*(involving U.S. Pat. Nos. 8,990,099, 9,037,479, 9,058,412, 9,058,413, 9,367,665, 9,734,294 and 9,805, 169), Case No. 2:17-cv-01041-ALM-CMV (S.D. Ohio), Jan. 3, 2019, 22 pages.

Electric Power Group v. Alstom, S.A., 830 F.3d 1350, 1353-54, 119 USPQ2d 1739, 1741-42 (Fed. Cir. 2016), p. 12.

Epstein et al., "Development of a Scheduled Drug Diversion Surveillance System Based on an Analysis of Atypical Drug Transactions", Anesthesia and Analgesia, Oct. 2007, vol. 105, No. 4, pp. 1053-1060.

\* cited by examiner

105

| Segment | Permissible Items | Quantity |
|---|---|---|
| Medicine Bottle 1 | Product A<br>Product B | 1 |
| Medicine Vial 2 | Product C<br>Product D<br>Product E | 3 |
| Medicine Bag 3 | Product F | 2 |
| Solution Bottle 4 | Product G<br>Product H | 3 |
| Etc. | . . . | . . . |

*Fig. 2B*

All Items by Segment 105

| Segment | Brand | Item/NDC/Lot | Strength | Expiration |
|---|---|---|---|---|
| Adenosine Vial | | Adenosine Injection NDC: 1001906302  Lot: 916136 | 6 mg/2 mL | Feb 28,2013 |
| | Adenosine Injection | Adenosine Injection NDC: 1001906302  Lot: 916136 | 6 mg/2 mL | Feb 28,2013 |
| | Adenosine Injection | Adenosine Injection NDC: 1001906302  Lot: 916136 | 6 mg/2 mL | Nov 30,2013 |
| Albuterol IPPB Sol. | Ipratropium Bromide And Albuterol Sulfate | Ipratropium Bromide and Albuterol Sulfate NDC: 0487-0201-60  Lot: 76AN1 | 3; .5mg/3mL; mg/3mL | Dec 31,2017 |
| | Ipratropium Bromide And Albuterol Sulfate | Ipratropium Bromide and Albuterol Sulfate NDC: 0487-0201-60  Lot: 76AN1 | 3; .5mg/3mL; mg/3mL | Dec 31,2017 |
| Albuterol MDI | VENTOLIN | VENTOLIN NDC: 0173-0682-54  Lot: 1ZP6940 | 108 ug/1 | Nov 30,2012 |
| Amiodarone Vial | Amiodarone Hydrochloride | Amiodarone Hydrochloride NDC: 67457-153-03  Lot: 101210 | 50 mg/mL | Oct 31,2012 |
| | Amiodarone Hydrochloride | Amiodarone Hydrochloride NDC: 67457-153-03  Lot: 101210 | 50 mg/mL | Oct 31,2012 |
| Atropine Bristojet | | Atropine NDC: 0548-3339-00  Lot: 1 | 1 mg/10 mL | Feb 28,2014 |
| | | Atropine NDC: 0548-3339-00  Lot: 1 | 1 mg/10 mL | Feb 28,2014 |
| Calcium Chloride Bristoject | | Calcium Chloride NDC: 0548-3304-00  Lot: BA00219 | 100 mg.mL | Aug 30,2012 |
| | | Calcium Chloride | 100 mg.mL | Aug 30,2012 |

Fig. 2C

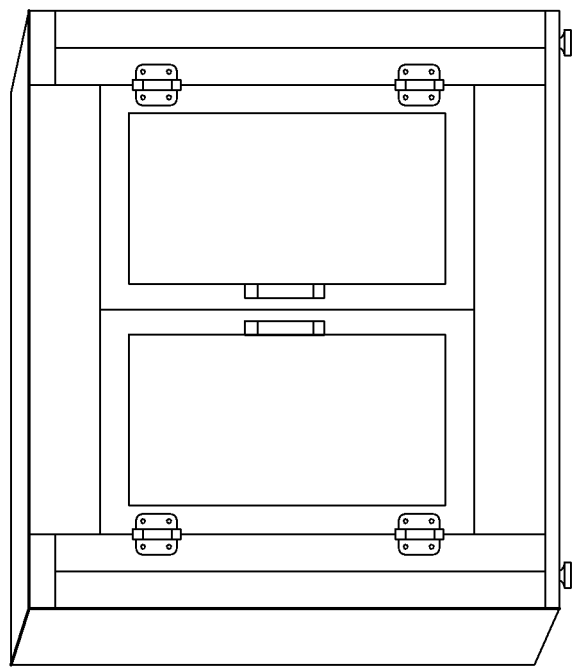
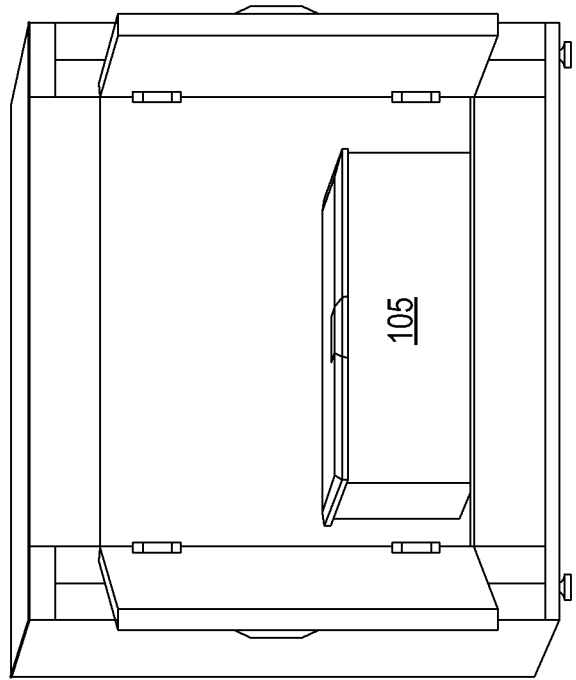
*Fig. 3B*

Pediatric Emergency Drug Tray | KitCheck-3
Drug Tray (3)

| 51 Total | | |
|---|---|---|
| 0 Extra | 1 Missing | |
| 0 Expired | 2 Expiring | |

⚡ Scan   ❖ Kits   📖 Reports   🏷 Print Tags

Procainamide Hydrochloride on October 1, 2012

Last Scan   September 28, 2012   Scan History | Details

Items Expiring Soon

| Manufacturer | Item | Size | Item Num (NDC) | Lot Num | Expiration |
|---|---|---|---|---|---|
| Hospira, Inc. | Procainamide Hydrochloride | 500 mg/mL | 0409-1903-01 | 1 | October 1, 2012 |
| Hospira, Inc. | Procainamide Hydrochloride | 500 mg/mL | 0409-1903-01 | 1 | October 1, 2012 |

Missing Items

| Shortage | Item | Expected | Actual |
|---|---|---|---|
| 1 | Magnesium Sulfate Vial | 2 | 1 |

*Fig. 10*

Demo Kit Tray (9) — 905, 1105

| 26 Total | 0 Extra | 1 Missing | 1 Expired | 1 Expiring |

Scan | Kits | Reports | Print Tags — 1135

Bill to KRE1981 — 1110

Central Pharmacy

[Check Out]

Protopic on September 28, 2012

Last Scan October 1, 2012  ▶ Show Scan History | Details — 1115

Expired Items — 1120

| Manufacturer | Item | Size | Lot Num | Expiration |
|---|---|---|---|---|
| Astellas | Protopic | 39487279 | 28841 | September 28, 2012 |

Items Expiring Soon — 1125

| Manufacturer | Item | Size | Item Num | Lot Num | Expiration |
|---|---|---|---|---|---|
| Alcon | Pataday Olopatadine Hydrochloride Opthalmic s | 1 Box | 650277224 | 174872F-1 | October 1, 2012 |

Extra Items — 1130

| Item | Expected | Actual | Surplus |
|---|---|---|---|
| Olopatadine Hydrochloride Opthalmic solution | 2 | 3 | 1 |
| Tacrolimus ointment 0.1% | 1 | 2 | 1 |

Kits that needs rework

Select a Report: Kits that needs rework ▶

☑ Surplus  ☑ Shortage  ☑ Expired  ☑ Expiring

☐ All Segments

Kits that needs rework

[Expand All] [Collapse All]

| Demo Kit | | Qty Expected | Item Num (NDC) | Lot Num | Expiration |
|---|---|---|---|---|---|
| Fluticasone Propionate Nasal Spray 50 Mcg | Shortage:1 | 2 | | | January 1, 2012 |
| Gentamicin Sulfate USP 0.3% | | 1 | | | November 3, 2012 ⚠ |
| Bandage Kit – Gauge and overpacked | | Qty Expected | Item Num (NDC) | Lot Num | Expiration |
| Large Bandages | Shortage:3 | 3 | | | |
| Medium Bandages | Shortage:3 | 3 | | | |
| Round Bandages | Shortage:3 | 3 | | | |

Select a Report: | Kits containing a specific item or lot number ▶ |

Manufacturer Name

Item Name

Item Number (NDC)

Lot Number | PAA32 |

─ 1305B

─ 1310B

Kits containing a specific item or lot number

| Demo Kit | | Item Num (NDC) | Lot Num | Expiration |
|---|---|---|---|---|
| Teva | ProAir HFA | 1 Box | 5931057920 | PAA32A | January 1, 2012 |

*Fig. 13B*

MANAGEMENT OF PHARMACY KITS

CROSS-REFERENCE TO RELATED APPLICATIONS

This application is a continuation of U.S. patent application Ser. No. 15/787,204, filed on Oct. 18, 2017, which is a continuation of U.S. patent application Ser. No. 14/701,958, filed on May 1, 2015, which is a continuation of U.S. patent application Ser. No. 14/603,730, filed on Jan. 23, 2015, which is a continuation of U.S. patent application Ser. No. 13/554,342, filed on Jul. 20, 2012, which claims priority to U.S. Provisional Application No. 61/514,231, filed on Aug. 2, 2011, each of which is incorporated herein by reference in its entirety.

BACKGROUND

Hospital pharmacies often manage groups of medical items in the form of pharmacy kits. A pharmacy kit can be used, for instance, to provide a group of items for a specific medical procedure, a particular physician, or a designated location of a hospital. As an example, a pharmacy kit can be used to aggregate and transport a collection of medicines for treating a patient with a specific type of stroke, heart condition, or other ailment.

A pharmacy kit (or "kit") typically comprises a group of items specified by a template. For example, the template may specify that the kit requires three vials of adenosine, two containers of albuterol solution, two vials of amiodarone, and so on. The template may also specify ways in which individual items may be satisfied. For example, it may specify that the vials of adenosine may be satisfied by certain product brands. Pharmacy kits are usually stocked by a hospital pharmacy, but they may be stocked by another entity, such as an outsourced kit stocking company.

Local board-of-pharmacy regulations (e.g., state regulations) typically allow a hospital or other facility to define the contents of its kits. In other words, they allow the hospital to create its own templates. These regulations, however, also require that the hospital adhere to a template once defined. This typically requires specific procedures to ensure accuracy of kit contents. Such procedures can include, for instance, regulated kit creation and inventory procedures, and prescribed monitoring and/or update procedures. The following are examples of such procedures as used in certain conventional contexts.

A kit is typically created by receiving specified items in a pharmacy, manually recording (e.g., on paper and/or electronic records) their product identifiers (e.g., National Drug Code (NDC) or Universal Product Code (UPC)), lot numbers, and expiration dates, and then loading the items into a container, such as a box, tray, or canister. During the kit's lifetime, it may be updated periodically to replace expired or consumed items. These updates are typically performed by manually inspecting the kit, comparing it to a corresponding template, modifying kit contents as required, and then manually recording any changes.

Unfortunately, the above procedures tend to suffer from significant shortcomings. For instance, the manual recording of item information is generally time consuming and error prone, which drives up the cost of creating and updating the kits. Moreover, these procedures are usually performed by highly trained pharmacy staff, which may be an inefficient use of their time. Manual inspections for missing, expired, or soon-to-be expired items can also be time consuming and error prone, particularly because item expiration dates tend to vary between different products within the same kit.

Due to the above and other shortcomings, there is a general need for improved techniques and technologies for managing pharmacy kits.

SUMMARY

According to one embodiment of the inventive concept, a system for managing pharmacy kits comprises a reading station configured to read tag information from a plurality of radio frequency identification (RFID) tags associated with a pharmacy kit, and an information processing system operatively connected to the reading station and configured to receive the tag information from the reading station and determine a status of the pharmacy kit based on the tag information, a plurality of stored templates defining contents to be included in each of a plurality of pharmacy kits, and a plurality of kit records indicating the current contents of a plurality of pharmacy kits.

According to another embodiment of the inventive concept, a method of managing pharmacy kits comprises operating an RFID reader to read tag information from a plurality of RFID tags associated with a pharmacy kit, identifying a plurality of items present in the pharmacy kit based on the tag information, and comparing the plurality of items with an electronic template to determine a status of the pharmacy kit.

According to another embodiment of the inventive concept, a method comprises building a pharmacy kit comprising a plurality of pharmaceutical items labeled with RFID tags, verifying contents of the pharmacy kit by operating an RFID reader to read tag information from the RFID tags and comparing the tag information with an electronic template, deploying the pharmacy kit within a facility following the verification, and re-verifying the contents of the pharmacy kit following the deployment by operating an RFID reader to read tag information from the RFID tags and comparing the tag information with the electronic template.

BRIEF DESCRIPTION OF THE DRAWINGS

The drawings illustrate selected embodiments of the inventive concept. In the drawings, like reference numbers indicate like features.

FIGS. 2A through 2C are diagrams illustrating a pharmacy kit according to an embodiment of the inventive concept.

FIGS. 3A and 3B are diagrams of a read station in the system of FIG. 1 according to an embodiment of the inventive concept.

FIG. 10 shows a report generated for a pharmacy kit using the system of FIG. 1 according to an embodiment of the inventive concept.

FIG. 11 shows another report generated for a pharmacy kit using the system of FIG. 1 according to an embodiment of the inventive concept.

FIGS. 13A and 13B show interfaces used to generate and view reports regarding pharmacy kits according to an embodiment of the inventive concept.

DETAILED DESCRIPTION

Figure 1:
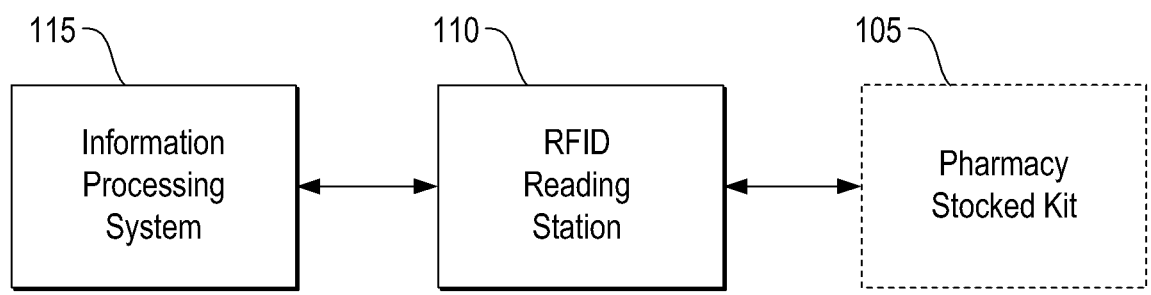
FIG. 1 is a block diagram of a system for managing pharmacy kits according to an embodiment of the inventive concept.

Embodiments of the inventive concept are described below with reference to the accompanying drawings. These embodiments are presented as teaching examples and should not be construed to limit the scope of the inventive concept.

The described embodiments relate generally to management of pharmacy kits (hereafter, "kits") such as those commonly used in hospital environments or other medical facilities. Such kits can be distinguished generally from other types of kits used by hospitals, such as surgical instrumentation kits, electronic equipment kits, and so on, due to the unique nature of pharmaceutical products. For example, pharmaceutical products may be regulated very different from the items in surgical kits due to the need to constantly monitor expiration dates, and also due to the substitutability of some pharmaceutical products for others.

In certain embodiments, a kit management system uses RFID technology to label and track the contents of a kit. The use of RFID technology can allow a pharmacy to accurately and efficiently determine whether items in the kit are consumed, missing, expired, or near expiration. These determinations can be used thereafter to verify and update the kit contents, track item usage patterns, generate patient billing information based on item consumption, and so on.

In certain embodiments, a hospital pharmacy begins by tagging items upon bulk receipt in the hospital, or when a kit is stocked. Alternatively, items may arrive at a hospital pre-tagged. One way to tag the items is by scanning bar codes present on most items used in a kit, printing RFID tags based on the scanned bar codes, and then applying the RFID tags to the items. The scanned bar codes typically provide item information such as product identifiers (e.g., NDC or UPC), lot numbers, and expiration dates. This information can be associated with the RFID tags in a computer database to allow subsequent identification and processing by RFID technology. In some embodiments, the RFID tags can be generated automatically when scanning the bar codes, e.g., through the use of an RFID tag printer operatively connected to a bar code scanning machine. Alternatively, the RFID tags may be non-printed tags.

A kit is typically built by placing tagged items in a container such as a box, tray, or canister, and optionally labeling the kit with an RFID tag having information such as a kit identifier, kit type, intended user, or location, for example. These steps are generally performed by a pharmacist or other competent medical professional.

Once a kit is built, its contents are verified by placing it in an RFID reading station, which reads all RFID tags within its sensing range to identify the kit type and any items present. In some embodiments, the RFID reading station includes an enclosure such as a metal box to allow scanning of the kit exclusive of other RFID devices that may be in the surrounding environment. Alternatively, the RFID reading station may omit such an enclosure, for instance, by performing reading in an open area such as table, or using a handheld RFID reader. If the kit has an RFID tag, the kit type can be determined from the tag. Otherwise, it may be inferred from the items present. Items are typically identified by recognizing their RFID tags and then accessing stored information that maps the RFID tags to specific item information.

The stored information may reside on electronic equipment located at the RFID reader station or a remote location such as a remote server, a personal computer (PC), a mobile device, etc. In addition to basic kit and item information, the electronic equipment may also store metadata related to kit processes, such as who built or rebuilt a kit, what items were replaced if the kit was restocked, when the items were inserted in the kit, when verification and update procedures were last performed or will next be performed, and so on.

After the kit and item information are determined by the kit management system, they are analyzed automatically with reference to one or more templates. For instance, a kit template may be located based on the kit type, and then the identified items may be compared with the kit template to determine whether any items are missing or require replacement based on use or expiration. Additionally, the information processing system may analyze item information to determine whether any items are expired or will soon expire. The kit can then be updated based on these analyses.

Kit templates are typically stored in a database within or associated with the information processing system. However, they can alternatively be stored within a memory associated within the RFID reading station or RFID reader, or they can be stored in a separate system accessible by the information processing system.

In general, expiration of an item may occur based on a fixed or variable timeframe. For example, some items may expire at a fixed date indicated by the manufacturer, while other items may expire after a certain amount of time out of the refrigerator, e.g., time of removal+X days. Whether the timeframe is fixed or variable can be indicated in the template at a master level for a particular item, or at a segment level for a segment including the item.

The automatic processing provided by RFID technology and associated electronic equipment allows kit management to be performed with greater efficiency and accuracy compared with conventional approaches. For instance, in some embodiments, kit contents and expiration dates can be validated in 15 seconds or less. Moreover, kit deficiencies can be reported to a pharmacist automatically, allowing them to be addressed in an efficient manner. This reporting can be accomplished, for instance, by an automatically generated charge sheet showing kit contents and expirations.

Once a kit is built and verified, it is ready to be sealed and deployed for use in the hospital. When a kit is used, the seal is broken and items may be removed or consumed. Accordingly, the kit may be subsequently returned to the RFID reading station for additional verification, monitoring, and updates. These additional procedures can be used, for example, to determine whether any items in the kit are missing (e.g., due to use), and whether any items are erroneously present in the kit. This information can then be used to generate a report indicating the status and any necessary updates for the kit, or for other purposes such as patient billing or supply ordering. Once the relevant information is collected, the kit can be rebuilt using the automatically generated report, and then redeployed for another use.

Stored item and kit information can also be used to perform various forms of monitoring and/or reporting related to inventory management. For instance, stored kit information can be analyzed to identify patterns of item consumption. Moreover, the stored information can be inspected to determine the location of kits containing expired items. These and other forms of monitoring and/or reporting can be performed either automatically or in response to user input. For instance, they can be performed according to a predetermined schedule or in response to certain event triggers. Alternatively, a user may simply request monitoring or a report as needed. For example, a pharmacy manager may log in to view consumption logs, usage logs, and current inventory to make more informed decisions on which inventory to keep and which kits may require special attention.

The kit management system typically further comprises a user interface and one or more software applications allowing a user to access information regarding the status of kits. As an example, a software application may be used to generate and print a kit charge sheet or charge sheet with the contents and expiration dates of the items and a kit. As other examples, a software application may be used to generate inventory reports showing where kits are dispatched within a hospital, an expiration report indicating dispatched items that are expired or near expiration, consumption, and usage reports with traceability to departments, code types, or patients. The kit management system can also comprise or be integrated with a real-time tracking system to maintain current information regarding kit locations. The real-time tracking system typically comprises electronic components associated with the kits and configured to transmit information from the kits to the information processing system to identify the kits' respective locations. Such tracking systems can also be combined with kit management software in order to update the information used to generate inventory reports.

As indicated by the foregoing, a kit management system according to certain embodiments can provide many potential benefits compared with conventional technologies. For example, the kit management system can provide more efficient verification and recording of kit contents, and more accurate monitoring of kits, items, and expiration dates. In certain embodiments, the kit management system may also provide data analysis capabilities for purposes such as patient billing, inventory tracking, and so on.

FIG. 1 is a block diagram of a system 100 for managing pharmacy kits according to an embodiment of the inventive concept.

Referring to FIG. 1, system 100 comprises an information processing system 115 and an RFID reading station 110. System 100 is configured to automatically read and process information from a pharmacy kit 105. This allows relatively efficient monitoring and updating of the kit's contents.

RFID reading station 110 comprises an RFID reader configured to read RFID tags located on kit 105. During a typical read operation, the RFID reader interrogates RFID tags associated with respective items in kit 105, and it also interrogates any RFID tag associated with kit 105. As a consequence of the interrogation, the RFID reader receives information identifying each tag, and it conveys the information to information processing system 115. Based on the tag information, information processing system 115 identifies kit 105 and the items present. This can be accomplished, for instance, by relating the tag information to item or kit information stored in a computer database.

Once the kit and items are identified, information processing system 115 may process corresponding information in various ways, for example, by displaying it to a user, generating reports indicating missing or expired items, performing patient billing procedures based on any consumed items, or merely storing it for subsequent analysis. In certain embodiments, the kit and item information is managed as a list. For example, it can be stored and accessed in the form of a list in a computer database or other storage medium.

System 100 may occasionally aggregate last known status information for each kit that has been read, and it may then determine whether any action is required to resolve expiration issues, missing item issues, or extra item issues in all of the kits in a hospital or other facility. These actions can be performed, for example, on a periodic basis, in response to particular events, or in response to a user request.

In addition to storing the current or most recent information regarding the kits, system 100 may also store a virtual history for each kit. Such a virtual history may include, for example, a record of each transaction involving the kit since the time it was tagged. Such transactions may include, for example, scans, database queries, updates such as restocking or removal of items, and so on. The virtual history may be maintained by information processing system 115, for example, and it may be output in the form of a report in response to a user request. In addition, the virtual history may be used to gather data or statistics that may be useful for planning future tasks such as kit updates, item restocking, and so on.

Kit 105 can be associated to a location or responsible person, such as a physician. This association can then be stored in system 100, and it can be used to quickly determine the location of kit 105 after deployment. The location of kit 105 can also be determined and/or updated by associating its RFID tag with a real time location system. In addition, kit 105 may be associated with a patient identifier or billing identifier and any missing items may be marked as being consumed by that billing or patient identifier. Such billing information may be stored either in system 100, in a separate system or in both system 100 and a separate system. System 100 may retrieve or update some or all of the billing information when a kit is read and items may or may not be consumed.

Where kit 105 contains prescription pharmaceuticals, the facility may be required to comply with requirements set by a state board of pharmacy. The precise regulations may vary from state to state, but can include requirements such as a mandatory visual inspection of kit 105 prior to deployment, or an item-by-item determination of each item type, lot number and expiration date. Other board of pharmacy requirements may include documentation to be included in kit 105 to verify completeness and accuracy of expiration data or a label on the outside of kit 105 to indicate the last check of the kit and the next expiring item in the kit.

In some embodiments, system 100 is configured to store relevant board of pharmacy requirements and verify that each step has been completed. System 100 can also be configured to compute steps automatically where allowed by regulations. Such steps may include, for example, printing documentation or labels, reading tags and verifying items, or requesting confirmation that a manual step has been completed. As these steps are completed, system 100 may record the name of the person who performed the steps. It may also confirm whether the person is authorized to perform the steps. In general, information regarding these and other steps can be recorded in system 100 using a log, database, or other storage format.

Although FIG. 1 shows RFID reading station 110 and information processing system 115 as separate features, they are not required to be physically or functionally separate. For instance, information processing features could be integrated with parts of RFID reading station 110, such as an RFID reader. In general, the physical and functional implementation of system 100 can be partitioned arbitrarily between various forms of hardware, software, firmware, etc., as will be recognized by those skilled in the art.

In addition, the physical and functional implementation of system 100 can be distributed arbitrarily across multiple devices, systems, or network components. For example, in some embodiments, information processing system 115 may include or be integrated with wireless mobile devices in order to convey information remotely. One potential use of such a configuration would be to transmit kit notifications to remote users via push email or SMS text messaging, or subscription based data feeds. Such notifications could be used, for instance, to alert users that an updated kit is available, that a kit should be returned to the pharmacy, that a checked-out kit requires updates due to item expiration, and so on. Another potential reason to integrate information processing system 115 with remote components is to receive updates of kit templates and item master data. For example, some or all of a kit template or item master data may be received from an external system. The received item master data could indicate, for example, that an item has been recalled or changed in some material respect.

Figure 2A:
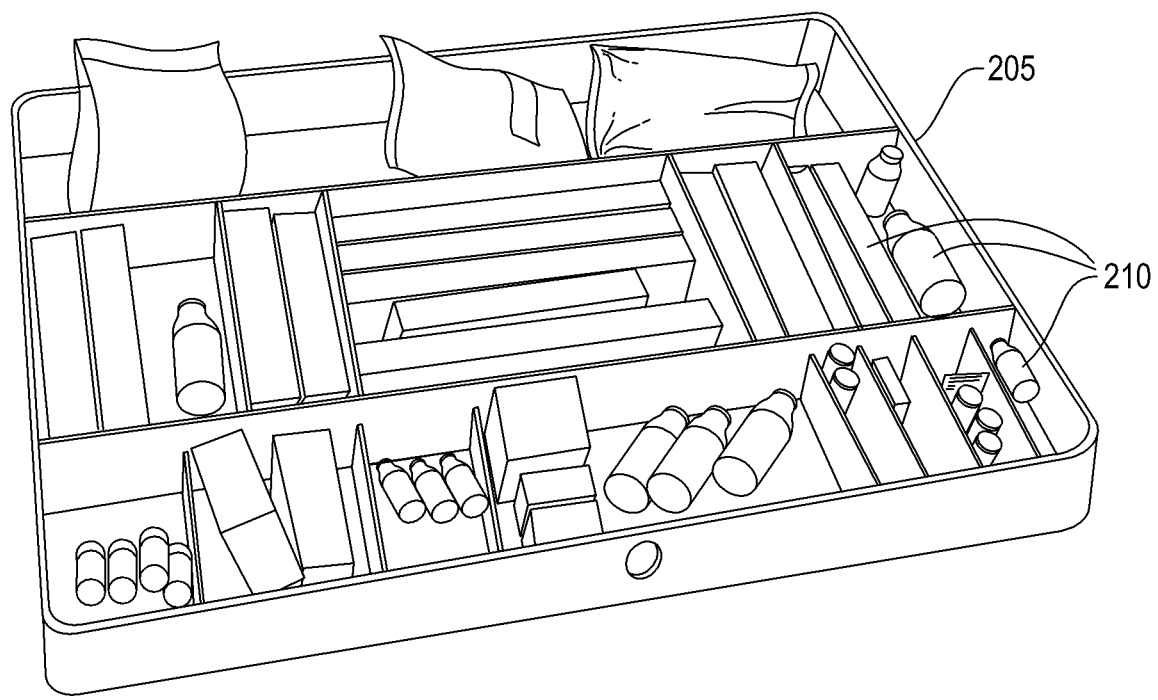

FIGS. 2A through 2C are diagrams illustrating a pharmacy kit according to an embodiment of the inventive concept. In particular, FIG. 2A shows an example of a kit tray comprising multiple items having RFID tags, FIG. 2B shows an example of a partial template associated with the kit, and FIG. 2C shows an example of a partial kit record for the kit. The kit of FIGS. 2A through 2C represents one example of pharmacy kit 105 shown in FIG. 1.

Referring to FIG. 2A, kit 105 comprises a container 205 and items 210. Container 205 is shown as a tray in FIG. 2A, but this is merely one example of a container that can be used to carry items 210. Alternative examples include boxes, canisters, bags, coolers, and various others. Although not shown in FIG. 2A, kit 105 could further comprise a cover, such as a lid, that can be used to enclose items 210 prior to deployment. Additionally, the cover can be sealed onto container 205 to prevent tampering between deployment and use of kit 105. In general, where kit 105 is susceptible to opening or closing (e.g., where it has a lid or other covering), it can be read in an open configuration or a closed configuration.

Items 210 typically include medicines or other medical supplies that may be stocked by a pharmacy. As shown in FIG. 2A, items 210 can have various different forms of packaging. For example, they can be packaged in vials, bags, boxes, bottles, and other forms. These different forms of packaging may also comprise different materials, such as glass, plastic, paper, cardboard, foam, or metal.

Due to the different types of packaging and materials, items 210 may be tagged with RFID tags having different shapes or types. As one example, RFID tags placed on metal bags may be subject to electromagnetic interference (EMI) from the metal. Accordingly, to prevent EMI, RFID tags connected to metal bags may have a foam backing or other form of insulation to create separation from the bags. Such tags may be referred to as metal-mount tags. As another example, RFID tags attached to small vials or bottles may potentially occlude label information on the vials. Accordingly, to prevent occlusion, RFID tags having a transparent adhesive portion may be attached to vials, bottles, or other types of packages. Such tags may be referred to as transparent tags.

Kit 105 is typically built by manually placing items 205 in container 210. This is typically accomplished by a pharmacist or other competent medical professional after items 205 have been labeled with RFID tags and stocked in the pharmacy. For example, a pharmacist may visit pharmacy shelves to collect items 205 and place them in container 210.

Referring to FIG. 2B, an example template defines items to be placed in kit 105. More specifically, the template defines a plurality of item segments (or "segments") to be included in kit 105, where each item segment corresponds to a class or type of items and/or additional segments to be included in specific quantities. For instance, an item segment may define a specific class of medications, such as ibuprofen, acetaminophen, adenosine, or albuterol. Where a segment includes one or more additional segments, the template is considered to have multiple segment "levels". In general, a template can have an arbitrary number of segment levels. An example of a template having multiple segment levels would be one containing a segment "analgesic", with the item "morphine" and a sub-segment "ibuprofen" containing items "Advil" and "Generic".

For simplicity, FIG. 2B shows example segments in generic form, i.e., "medicine bottle 1", "medicine vial 2", etc. The segment "medicine bottle 1", for example, indicates that kit 105 is to include one or more bottles of a first type of medicine (e.g., a bottle of ibuprofen). Similarly, the segment "medicine vial 2" indicates that kit 105 is to include one or more vials of a second type of medicine (e.g., a vial of adenosine), and so on. Although each segment in FIG. 2B is associated with a particular type of packaging, such as a bottle, vial, or bag, segments are not necessarily limited by package type. For instance, a segment could be defined more broadly based on medicine type alone.

The template further defines a set of permissible items that can be used to satisfy each segment. The permissible items may correspond to different brands or other forms of each item corresponding to the segment. These items are generally identifiable by distinct NDC or UPC identifiers. As an example, a segment defined as a "bottle of ibuprofen" may be satisfied by a either a bottle of Advil or a bottle of generic ibuprofen. For simplicity, FIG. 2B shows the items associated with each segment in generic form, i.e., "product A", "product B", etc. Accordingly, the segment "medicine bottle 1" may be satisfied by two different products "A" and "B", the segment "medicine vial 2" may be satisfied by three different products "C", "D", and "E", and so on.

The template still further defines a quantity of items to be included in kit 105 for each segment. For example, based on the template of FIG. 2B, kit 105 is to include one item corresponding to "medicine bottle 1" (e.g., one bottle of ibuprofen), three items corresponding to "medicine vial 2", two items corresponding to "medicine bag 3", and so on. As a more concrete example, a segment "Pain Medication" could have permissible items "Tylenol" or "Advil", with a quantity of two, which could be satisfied by two bottles of Tylenol, two bottles of Advil, or one of each, for instance.

In general, the quantity can be zero or more. Where the quantity is greater than one, each item of a particular segment can be satisfied by any combination of the permissible items for that segment. For example, if there are three permissible items and the required quantity is three, the requirement may be satisfied by three of the same permissible item, one of each, etc. For instance, some kits may allow the stock of adenosine vials to be satisfied by different product brands. Alternatively, the template may require that multiple instances of the same item be selected, or that only certain combinations of items are permitted. Moreover, the template may include restrictions on the items that can be included in combination from among different segments.

Although the template determines the contents to be included in the kit under most circumstances, there are occasions where deviation from the template will be permitted. One of these occasions is a national shortage of one or more items to be included in the kit. When there is a national shortage of a particular item, certain substitutions or omissions of the item may be allowed. For example, if sodium bicarbonate is on national shortage, a kit may be permitted to include a suitable substitute for sodium bicarbonate, or it may be permitted to be deployed without sodium bicarbonate or any substitute.

The procedure for managing items under shortage may be defined in a variety of ways. For example, allowable substitutes for national shortage conditions may be embedded in the template itself and then triggered by information processing system 115 when a shortage arises. As an alternative example, information processing system 115 may simply ignore certain restrictions in a template when a shortage arises.

Referring to FIG. 2C, a kit record comprises information regarding the contents of a kit that has been built in a pharmacy and verified through the use of RFID reading station 110. In the example of FIG. 2C, the information comprises the name of each segment in the kit, and specific details of each item in each segment. The specific item details include a brand name, an item name, an NDC identifier, a lot number, medicine strength or concentration, and an expiration date. The item details may further include information indicating whether an item has a fixed expiration date or one that varies based on time away from a refrigerator. Where the item has a variable expiration date, the item details may indicate whether the item has been removed from the refrigerator, and if so, at what time or date.

The kit record is typically generated by RFID reading station 110 or information processing system 115 upon verifying or re-verifying the kit. It can then be compared to a corresponding template to determine whether the kit has missing or expired items, or it can be stored in information processing system 115 for subsequent comparisons, updates, or analyses.

Figure 3A:
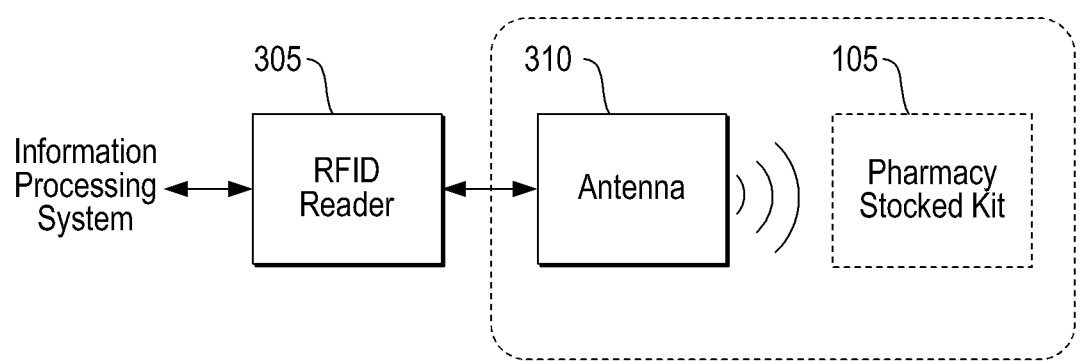

FIGS. 3A and 3B are diagrams of RFID reading station 110 of FIG. 1 according to an embodiment of the inventive concept. In particular, FIG. 3A is a block diagram illustrating electronic equipment associated with RFID reading station 110 according to an example embodiment, and FIG. 3B is a schematic diagram of a container configured to receive kit 105 during a read operation of RFID reading station 110.

Referring to FIG. 3A, RFID reading station 110 comprises an RFID reader 305 and an antenna 310. Antenna 310 is located within a container 315 designed to receive kit 105 during a read operation. RFID reader 305 controls antenna 310 to communicate with RFID tags associated with items of kit 105, as well as any RFID tag associated with the kit itself. In addition, RFID reader 305 receives and processes communications received by antenna 310 from kit 105.

Although RFID reader 305 is shown outside of container 315, it could alternatively be included within container 315. Moreover, although RFID reader 305 and antenna 310 are shown as two separate components, they could alternatively be integrated into a single component or divided into additional components.

In a typical read operation, RFID reader 305 controls antenna 310 to interrogate any RFID tags within container 315. In response to the interrogation, the RFID tags communicate information to RFID reader 305 via antenna 310. The communicated information is typically associated with corresponding information stored in a database, such as NDC identifiers, lot numbers, and expiration dates for individual items, and a kit identifier for the kit as a whole. RFID reader 305 communicates the received information to information processing system 115 for storage and/or comparison with a template.

Referring to FIG. 3B, container 315 comprises an enclosed space for receiving kit 105. The left side of FIG. 3B shows container 315 with doors opened to receive kit 105, and the right side of FIG. 3B shows container 315 with doors closed to perform a read operation. The use of an enclosed space to allows RFID tags to be read without interference from objects in the surrounding environment, such as false positives from RFID tags on items not belonging to kit 105. Accordingly, container 315 may be formed of a material designed to provide electromagnetic shielding, such as a metal box.

In some embodiments, RFID reading station 110 is restricted to receiving only one kit at a time. This restriction may be imposed in a variety of ways, for instance, by configuring an enclosure to accommodate only one kit container or interrogating kit tags prior to scanning to ensure that no more than one kit tag is present. In certain alternative embodiments, RFID reading station 110 may be specifically configured to allow concurrent scanning of multiple kits. For example, two kits could be placed in RFID reading station 110, scanned concurrently, and then assigned to a common location or person, such as a particular cart, room, physician, etc. Moreover, such a common assignment may be recorded in information processing system 115 to allow joint analysis or tracking of more than one kit.

Figure 4:
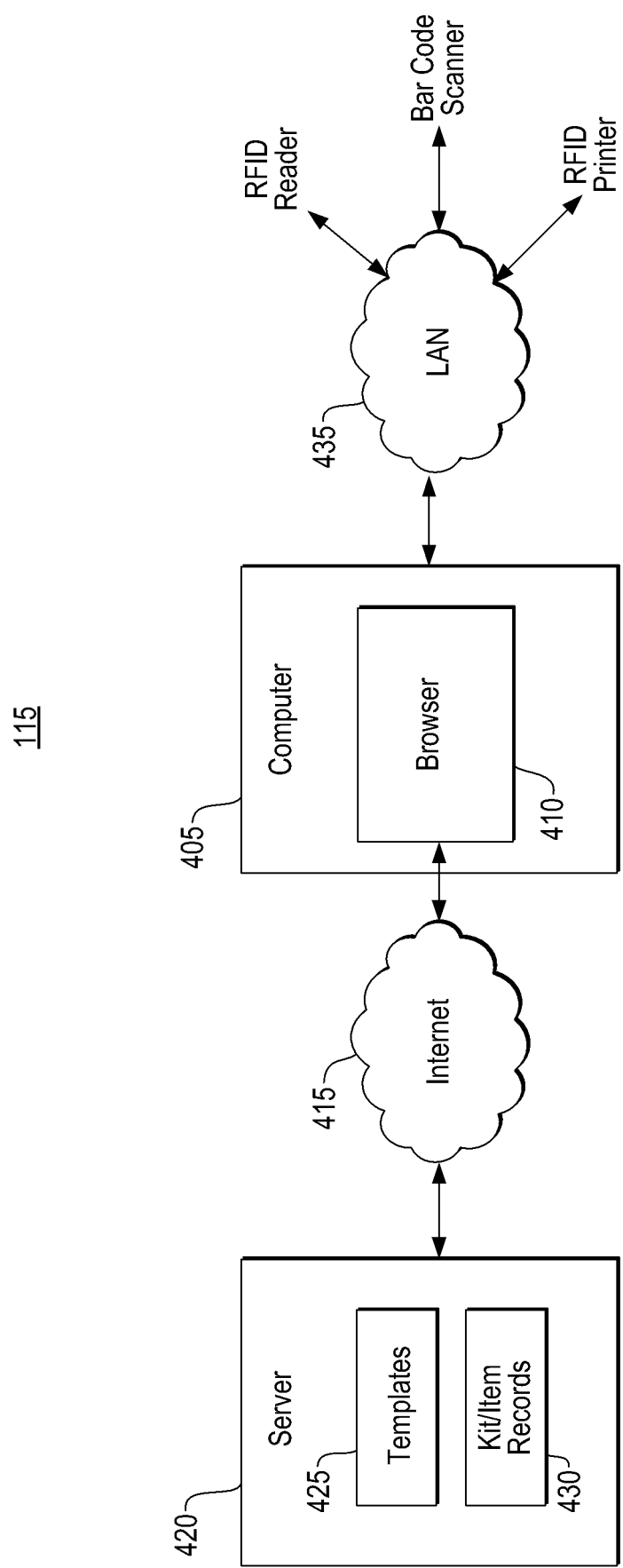
FIG. 4 is a diagram of an information processing system in the system of FIG. 1 according to an embodiment of the inventive concept.

FIG. 4 is a diagram of information processing system 115 according to an embodiment of the inventive concept. In the embodiment of FIG. 4, various features of information processing system 115 are connected in a networked configuration. However, in alternative embodiments these components could be in alternative configurations, e.g., with components directly connected, physically integrated, or functionally partitioned in other ways.

Referring to FIG. 4, information processing system 115 comprises a computer 405 and a server 420. Computer 405 and server 420 are connected to each other via the internet 415, and computer 405 is connected to an RFID reader, a bar code reader, and an RFID printer through a local area network (LAN) 435.

Computer 405 comprises a browser 410 that receives kit information from the RFID reader via LAN 435 and communicates with server 420 through the internet 415. Server 420 stores templates 425, which typically include kit master templates and item master templates. Server 420 also stores records 430, which include information regarding individual kits and items.

Although server 420 is shown as a single unit in FIG. 4, it may comprise more than one device, such as multiple local and/or central computers. In addition, although server 420 is shown to be connected with a single computer, it may be connected to additional or alternative devices, such as other local computers, mobile devices, and so on. Moreover, although server 420 is shown to receive information from a single RFID reader, it could also receive information from other RFID readers. For example, information processing system could be connected to multiple RFID reading stations through the internet 415.

The RFID printer can be used to print RFID tags automatically when a kit is being built or updated. For example, an RFID tag can be printed for a new item by scanning the item's bar code using a bar code scanner connected to computer 405, accessing server 420 to associate a particular RFID tag with the item, and then printing the RFID tag.

Figure 5:
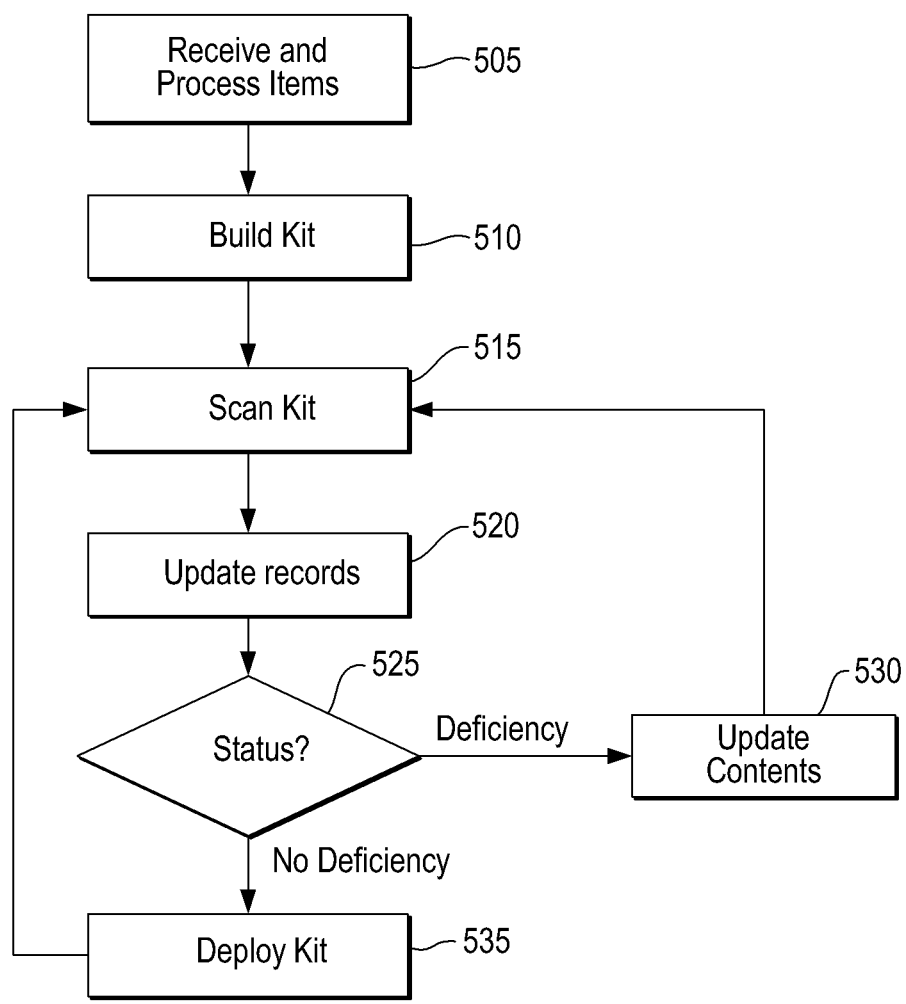
FIG. 5 is a flowchart illustrating a method of managing pharmacy kits according to an embodiment of the inventive concept.

FIG. 5 is a flowchart illustrating a method of managing pharmacy kits according to an embodiment of the inventive concept. The method of FIG. 5 is typically performed by a pharmacist or other medical professional associated with a hospital pharmacy. For explanation purposes, it will be assumed that the method of FIG. 5 is performed using system 100 of FIG. 1. However, the method is not limited to a particular system. In the description that follows, example method steps will be indicated by parentheses (XXX) to distinguish them from device or system components.

Referring to FIG. 5, the method begins with a pharmacy receiving and processing kit items (505). The items typically arrive in bulk at the pharmacy and are processed by tagging them with RFID tags and recording them in an inventory system. Next, a kit is built from tagged items in the pharmacy inventory (510), and the kit is scanned using RFID reading station 110 (515). The scan detects RFID tags of kit items and the kit itself and transmits corresponding information to information processing system 115.

Information processing system 115 updates stored records to reflect the scanning (520). In the update, a database in information processing system 115 is updated to reflect the scanned kit contents. For example, the database may be updated to reflect the presence of any new or replaced items, along with their expiration dates. The database may also be updated with other information, such as the name of the person who last modified the kit contents, a location to which the kit is to be deployed, a patient to be billed for consumption of kit items, and so on.

Based on the updated records, information processing system 115 performs a status check to verify the contents of the kit (525). The status check typically involves forming a list of items based on the transmitted information or updated records and comparing the list against a kit template. It may also involve comparing the updated kit information against information obtained in prior scans, or evaluating the kit information in light of certain business rules, such as billing protocols.

If the status check indicates a deficiency in the kit (525="Deficiency"), such as missing or expired items, the kit contents are updated (530), and the method returns to step 515 where the kit is re-scanned. The update can be performed, for example, by replacing any expired items or inserting missing items. Otherwise, if the status check indicates no deficiency in the kit (525="No Deficiency"), the kit is deployed for use in the hospital or other facility served by the pharmacy (535).

The updating of records and status check are typically performed any time the kit is scanned, as indicated by the flow of FIG. 5. This can take place under a variety of circumstances, such as when a kit is first built and verified, when the kit is checked-in to the pharmacy for storage, or when the kit is checked-out of the pharmacy for use.

Deployment of the kit may involve, for example, transporting it to a specific location of the hospital, checking it out to a particular individual, or merely storing it within the pharmacy. Following deployment, steps 515 through 535 may be repeated any number of times as needed. For example, the kit may be re-scanned and updated following each use or it may be periodically updated at specified times, such as daily, weekly, or whenever an expired item is noted in information processing system 115.

Figure 6:
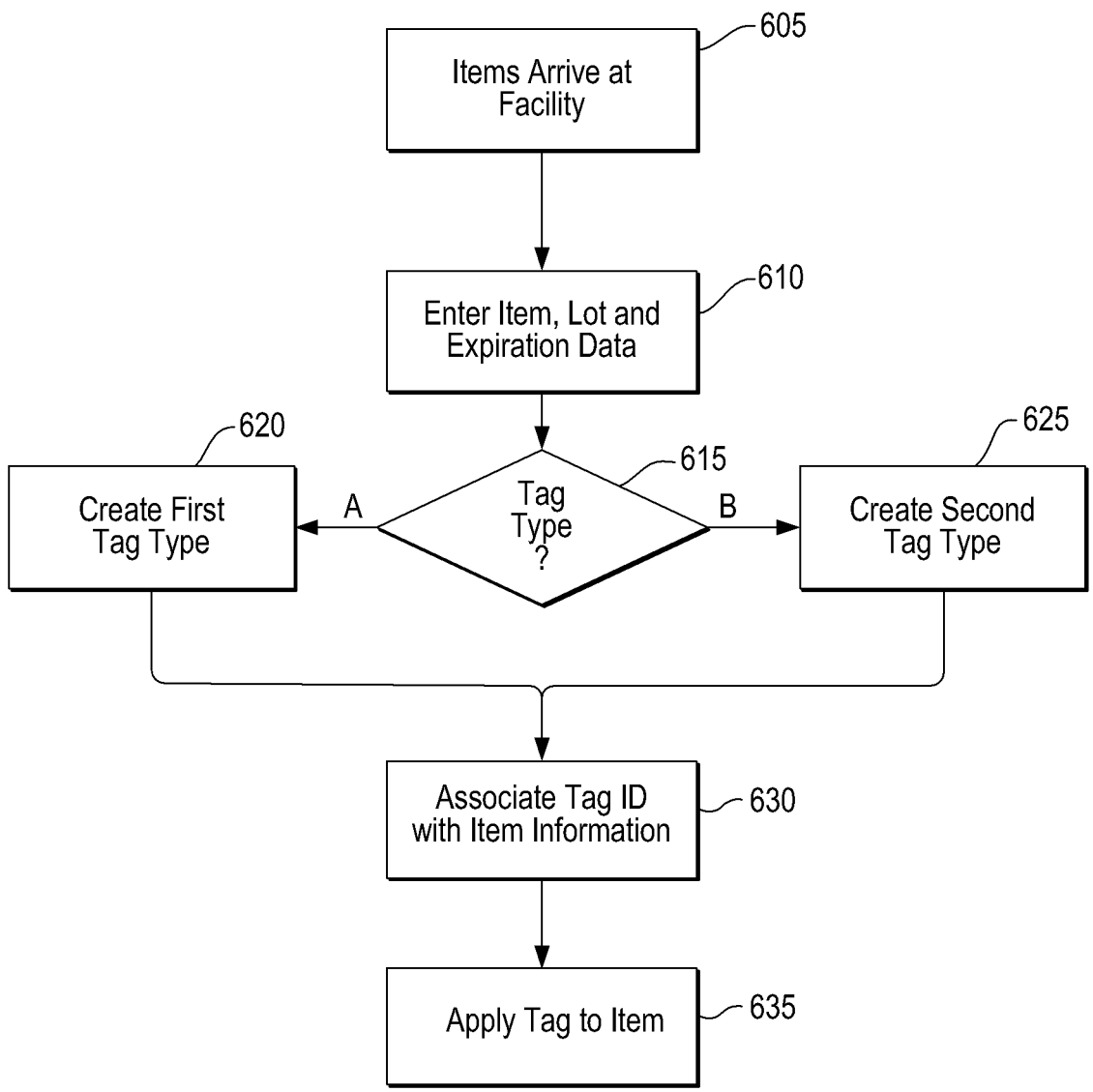
FIG. 6 is a flowchart illustrating a method of receiving and processing items for a pharmacy kit according to an embodiment of the inventive concept.

FIG. 6 is a flowchart illustrating a method of receiving and processing items for a pharmacy kit according to an embodiment of the inventive concept. The method of FIG. 6 is an example of step 505 of FIG. 5.

Referring to FIG. 6, items arrive at a facility (e.g., a hospital) from a third party manufacturer, distributor, or supplier (605). In some circumstances, the items may have RFID tags when they arrive at the facility. Accordingly, system 100 may scan the items and look up item information from the third party or an additional third party. Such information may include, for example, item master data, item lot data, and item expiration dates. If the items are not already tagged, item information may be entered into system 100 using a bar code scanner as described above, or by manual user input (610).

Based on the item information, system 100 determines whether each item requires a first type of tag (illustrated as type "A") or a second type of tag (illustrated as item type "B") (615). This determination is typically performed based on the type of the item or its packaging. For example, items having metal packaging such as metal bag, etc., may require an RFID tag having a thicker insulation layer (e.g., foam) to prevent it from experiencing EMI from the metal. Other types of items, such as glass or plastic packages, may not require such an RFID tag. Although the method of FIG. 6 shows an example using two different tag types, the described method is not limited to two tag types, and could be performed with additional tag types. Following the determination of the tag type, system 100 creates the first type of tag (620) or the second type of tag (625).

In creating the tags, system 100 may optionally perform automatic detection of whether it is attached to an RFID printer. If such an attachment is detected, it may control the RFID printer to print an RFID tag having a unique identifier for each item in the kit. Otherwise, a user may manually enter a unique tag identifier for each item into system 100. The manually entered identifiers can be determined, for example, based on the labeling of already printed RFID tags.

Next, system 100 associates the unique identifiers with the stored item information (630), allowing the item information to be retrieved subsequently when the RFID tags are scanned. Finally, the RFID tags are attached to corresponding items (635).

Figure 7:
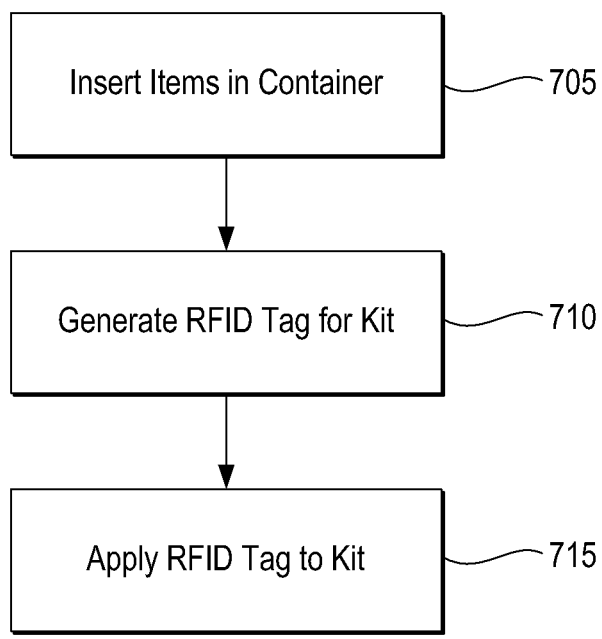
FIG. 7 is a flowchart illustrating a method of building a pharmacy kit according to an embodiment of the inventive concept.

FIG. 7 is a flowchart illustrating a method of building a pharmacy kit according to an embodiment of the inventive concept. The method of FIG. 7 is an example of step 510 of FIG. 5.

Referring to FIG. 7, the method comprises inserting tagged items into a container (705), generating an RFID tag for the kit (710), and applying the RFID tag to the kit (715). The method may further comprise sealing the kit; however, the sealing is typically performed after the kit has been scanned. Where system 100 is connected to an RFID printer, the kit's RFID tag can be generated using the printer, similar to the method of FIG. 6. Otherwise, a preprinted RFID tag can be used, and the tag's number can be manually entered into system 100 as in the method of FIG. 6. The sealing can be performed, for example, using a shrink wrap material, an adhesive, a sticker, or various other known techniques. In general, the term seal or sealing, as used herein, should not be construed in an overly formal sense—for example, it does not require an airtight seal—but rather it merely refers to a mechanism for ensuring that the contents of the kit are not tampered with as long as a seal remains in place or unbroken. Moreover, some seals used in conjunction with RFID technology may allow RFID based detection of whether a seal is broken.

Figure 8A:
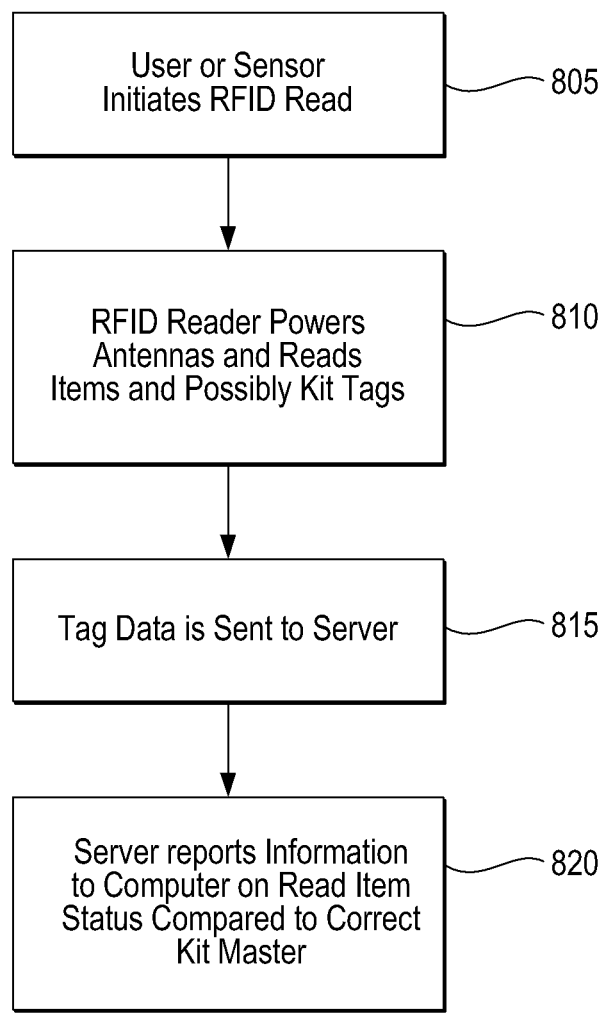
FIGS. 8A and 8B are flowcharts illustrating methods of operating the system of FIG. 1 according to an embodiment of the inventive concept.
Figure 8B:
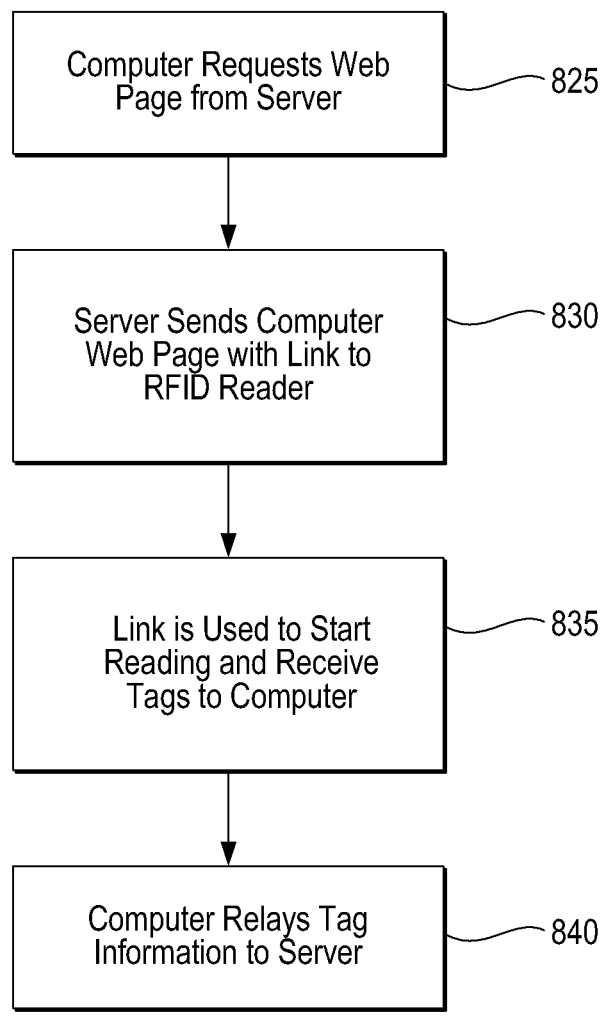

FIGS. 8A and 8B are flowcharts illustrating methods of operating kit management system 100 according to an embodiment of the inventive concept. In particular, FIG. 8A shows a method that can be used to implement step 515 of FIG. 5, and FIG. 8B shows a method that can be used to implement parts of the method of FIG. 8A.

Referring to FIG. 8A, a user or sensor initiates an RFID read operation (805). This can be accomplished, for instance, by merely placing kit 105 in RFID reading station 115, or by actuating specific controls on a user interface. In the read operation, RFID reader 305 powers antennas of RFID tags in kit 105, and it reads item tags and a kit tag, if present (810). The read operation may be used to perform an initial inventory of kit 105 following its assembly, or it can used for a re-inventory following use. Next, tag data is sent to a server in information processing system 115 or elsewhere (815). Finally, the server reports information to a user via an interface such as a computer display or a computer-generated printout (820).

Referring to FIG. 8B, steps 805 and 815 can be performed through the use of a web interface such as a web browser. For example, in some embodiments, a user directs a computer to request a web page from a server (825). This is typically accomplished through a web browser and it can be done in an encrypted or non-encrypted manner. For instance, the computer can communicate with the server using an encrypted protocol such as the secure sockets layer (SSL) protocol.

Next, the server returns instructions on how to scan which could take the form of a link allowing control of the RFID reader (830). In the example using a link, the user clicks on the link to start a read operation, and the RFID reader then captures tag information from kit 105 and transmits it to the computer (835). Finally, the computer relays the tag information to the server for validation, storage, and/or other forms of processing (840).

The server typically stores kit-related information such as master templates, item master templates, and information regarding individual kits and items, as in the example of FIG. 4. This information can be compared with the tag information relayed to the server in step 840, and then based on the comparison the server may generate a report on the status of the kit, such as whether any items are absent or whether any items have been erroneously included in the kit. The report may also include information relating to the expiration status of the items in kit 105, such as whether the items are expired or near expiration, or a summary of the expiration status of a set of items or the kit as a whole. The report may also include a charge sheet including the status of each item, such as its expiration date, which items have expired, which items are about to expire, and which item is going to expire next. In general, the information included in the report may be data that was read from a kit, item, or other source, or it may be data that was calculated based on rules, inputs, or other criteria.

Figure 9:
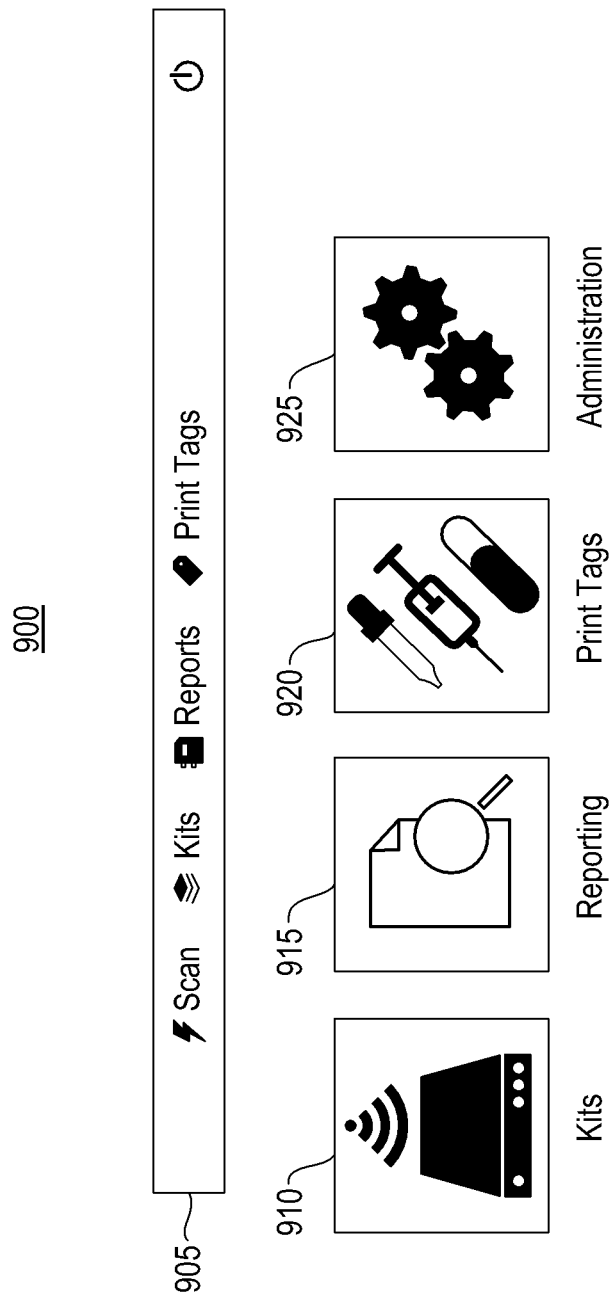
FIG. 9 shows an interface that can be used to control the system of FIG. 1 according to an embodiment of the inventive concept.

FIG. 9 shows an interface 900 that can be used to control system 100 according to an embodiment of the inventive concept. For example, interface 900 can be used to control various aspects of the methods illustrated in FIGS. 5 through 8. Interface 900 is typically accessed through a display connected to a computer or server such as those illustrated in FIG. 4.

Referring to FIG. 9, interface 900 comprises interactive graphical user interface (GUI) components including a menu bar 905 and buttons 910 through 925. These features allow a user to initiate various kit-related procedures, such as scanning a kit that has been placed in an RFID reading station, generating reports based on kit information, printing RFID tags for a kit, and performing administrative tasks. For example, a user may press button 910 (or alternatively, a scan button in menu bar 905) to initiate a read operation of RFID reading station 110 after kit 105 has been placed in a designated reading location such as a metal box. The user may press button 915 to generate a report comprising information similar to that illustrated in FIG. 2C. The user may press button 920 to initiate a procedure for capturing item information and printing RFID tags. Finally, the user may press button 925 to access various administrative controls for system 100 or interface 900.

FIG. 10 shows a report 1000 generated for a pharmacy kit using system 100 according to an embodiment of the inventive concept. Report 1000 corresponds to a pediatric emergency drug tray, which is a type of kit comprising items used for common pediatric emergencies. Such a kit can be deployed to a hospital emergency room, for example.

Referring to FIG. 10, report 1000 comprises a portion 1005 indicating the type of kit for which the report was generated, as well as the total number of items in the kit. In this example, the kit comprises 51 total items. Report 1000 further comprises a portion 1010 indicating the number of extra and missing items in the kit, as well as the number of expired or soon to expire items. In this example, one item is missing and two items are near expiration. The soon-to-expire items are listed as two containers of Procainamide Hydrochloride, which expire on Oct. 1, 2012. The date range of soon-to-expire items can be set arbitrarily, for example, using administrative tools accessible through button 925 in interface 900. Nevertheless, the date range is typically established in consideration of factors such as the anticipated delay between deployment of the kit and its use, as well as any regulatory considerations, such as rules from the board-of-pharmacy requirements or the joint commission (TJC).

Report 1000 also includes a portion 1015 indicating the date of a most recent scan, a portion 1020 showing additional details for the soon-to-expire items, and a portion 1025 showing additional details for missing items.

FIG. 11 shows another report 1100 generated for a pharmacy kit using system 100 according to an embodiment of the inventive concept. Report 1100 corresponds to a demonstration kit, which is a type of kit comprising items used for common pediatric emergencies. Such a kit can be deployed to a hospital emergency room, for example.

Report 1100 comprises a portion 1105 indicating the type of the kit and the total number of items in the kit. In this example, the kit comprises 26 total items. Report 1100 further comprises a portion 1010 indicating the number of extra and missing items in the kit, an entity to be billed for used items, and the number of expired or soon to expire items. In this example, there are two extra items, one expired item, and one soon-to-expire item. The entity to be billed is listed as KRE1981. The expired item is a box of Protopic, which is listed as having expired on Sep. 28, 2012.

Report 1100 further comprises a portion 1115 indicating the date of a most recent scan, a portion 1120 showing additional details for the expired items, a portion 1125 showing additional details for the soon-to-expire items, and a portion 1130 showing additional details for the extra items. Report 1100 still further comprises a portion 1135 indicating a current location of the kit and providing a "check out" button for assigning the kit to a specific location or person. In this example, the kit is currently assigned to the location "Central Pharmacy".

Figure 12:
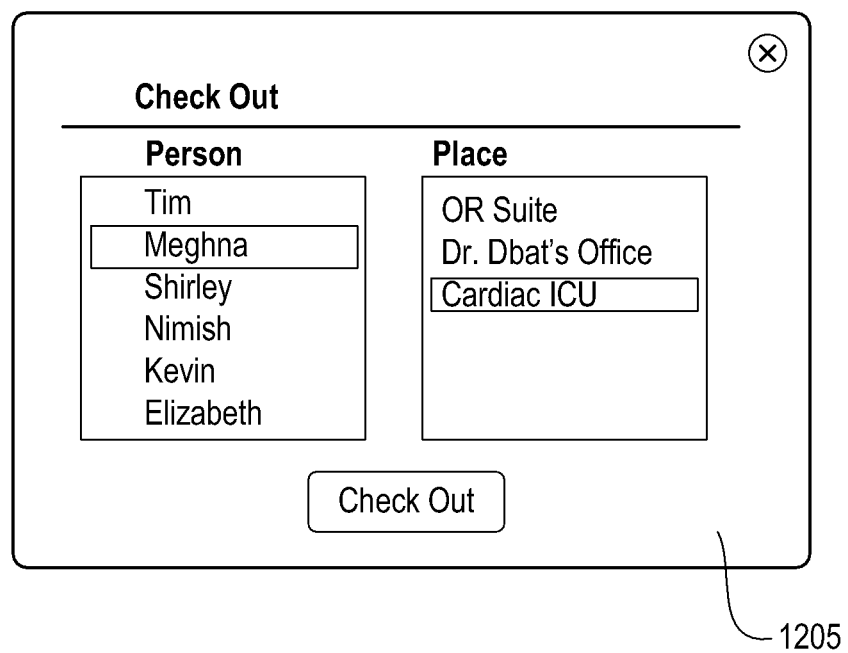
FIG. 12 shows an interface for checking out a kit to a user or location according to an embodiment of the inventive concept.

FIG. 12 shows an interface 1200 for checking out a kit to a user or location according to an embodiment of the inventive concept. Interface 1200 can be invoked, for instance, using the check out button in area 1135 of FIG. 11. In response to a user pressing the check out button, a dialog box 1205 appears within interface 1200. Dialog box 1205 allows a user to select a person or place to whom the kit may be assigned. This selection can be made, for example, as the kit is placed in possession of the selected person or an authorized delivery agent. Information regarding the selected person and location can then be stored in system 100 to facilitate subsequent recovery or further monitoring of the kit.

FIGS. 13A and 13B show interfaces 1300A and 1300B used to generate and view reports for pharmacy kits according to an embodiment of the inventive concept. In particular, FIG. 13A shows an example of an interface where a user has selected to view a report of kits that need re-working, and FIG. 13B shows an example of an interface where a user has selected to view a report of kits containing a specific lot number.

Referring to FIG. 13A, interface 1300A comprises a first area 1305A where a user selects a type of report to be generated. In this example, the user has selected from a drop down menu to generate a report of kits that need re-working. Once the selection is made the drop down menu, first area 1305A is further populated with options of details to include in the report. In this example, the options allow the user to select whether the report should include surplus items, shortages, expired items, expiring items, or all segments of the kit.

Interface 1300A further comprises a second area 1310A for displaying the report. According to the report in area 1310A, system 100 has information on two kits satisfying the specified options. In particular, a demo kit has a shortage of nasal spray, and it has a soon-to-expire container of Gentamicin Sulfate. A bandage kit has shortages of small, medium, and large bandages.

Referring to FIG. 13B, interface 1300B comprises a first area 1305B where a user selects the type of report to be generated. In this example, the user has selected from the drop down menu to generate a report of kits containing a specific item or lot number. Based on this selection, first area 1305B is populated with a form allowing the user to enter all or part of a lot number or other information for identifying the item. In the example of FIG. 13B, the user has entered a lot number.

Interface 1300B further comprises a second area 1310B for displaying the report. According to the report in area 1310B, a demo kit includes an item with the lot number specified in second area 1310A. Notably, in the example of FIG. 13B, only a partial lot number is entered first area 1310B, so second area 1310B displays information related to items that begin with the partial lot number. However, system 100 could be modified to use the exact lot number only. It could also be modified to use multiple lot numbers.

In addition to generating reports such as those illustrated in FIGS. 10 through 13, system 100 may also generate reports on kit locations. Such locations can be determined, for example, through automatic kit tracking or some other mechanism. Moreover, system 100 may also provide mechanisms for automatically tracking inventory in the kits and the usage of items based on usage data. For example, by analyzing usage data of different items, system 100 could determine the level inventory to meet minimum requirements of all kits in a facility or a target level of inventory to be maintained. For example, if a type of kit requires a bottle of ibuprofen and the facility has 20 kits of that type, the facility has a minimum requirement of 20 bottles of ibuprofen. If the facility uses 10 bottles of ibuprofen during a specified time (e.g., a month), system 100 could then estimate or predict when the facility will run out of the current stock of ibuprofen. Accordingly, system 100 can be used to predict where inventory shortages may occur and then alert relevant personnel of potential existing or upcoming inventory shortages.

System 100 may also automatically inventory items in pharmacy kits to determine where anything is missing, extra, expired, or near expired. This can reduce the chance of manual kit stocking errors or related medical errors in a hospital or other facility. System 100 may also automatically find items for recall in the hospital or emergency medical field kits.

Figure 14A:
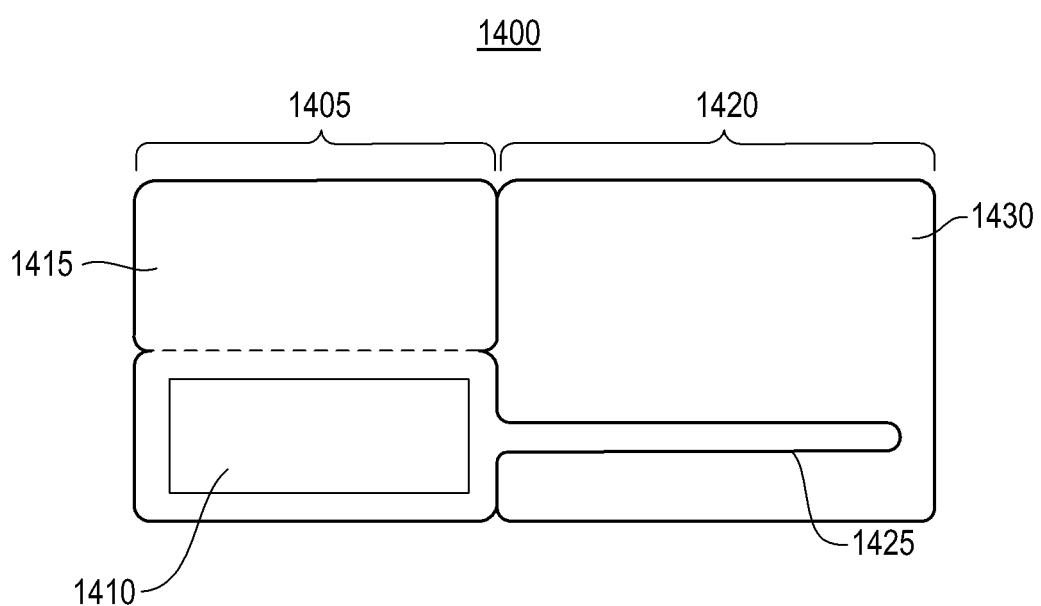
FIGS. 14A through 14D are diagrams of a label that can be used to attach an RFID tag to various items of a pharmacy kit according to an embodiment of the inventive concept.
Figure 14B:
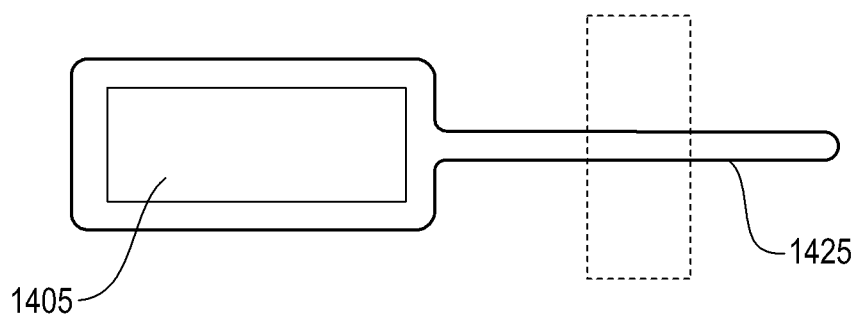
Figure 14C:
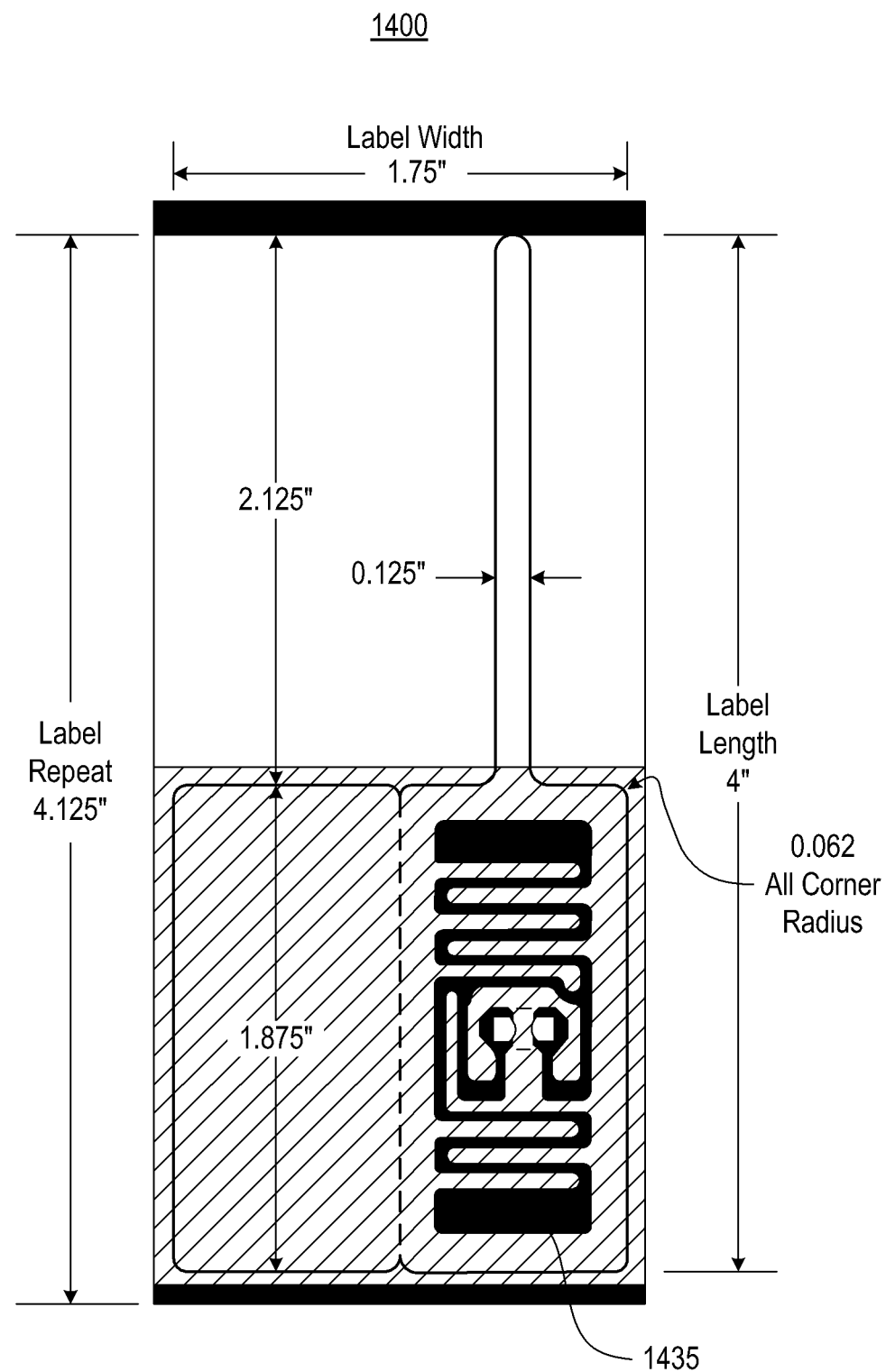
Figure 14D:
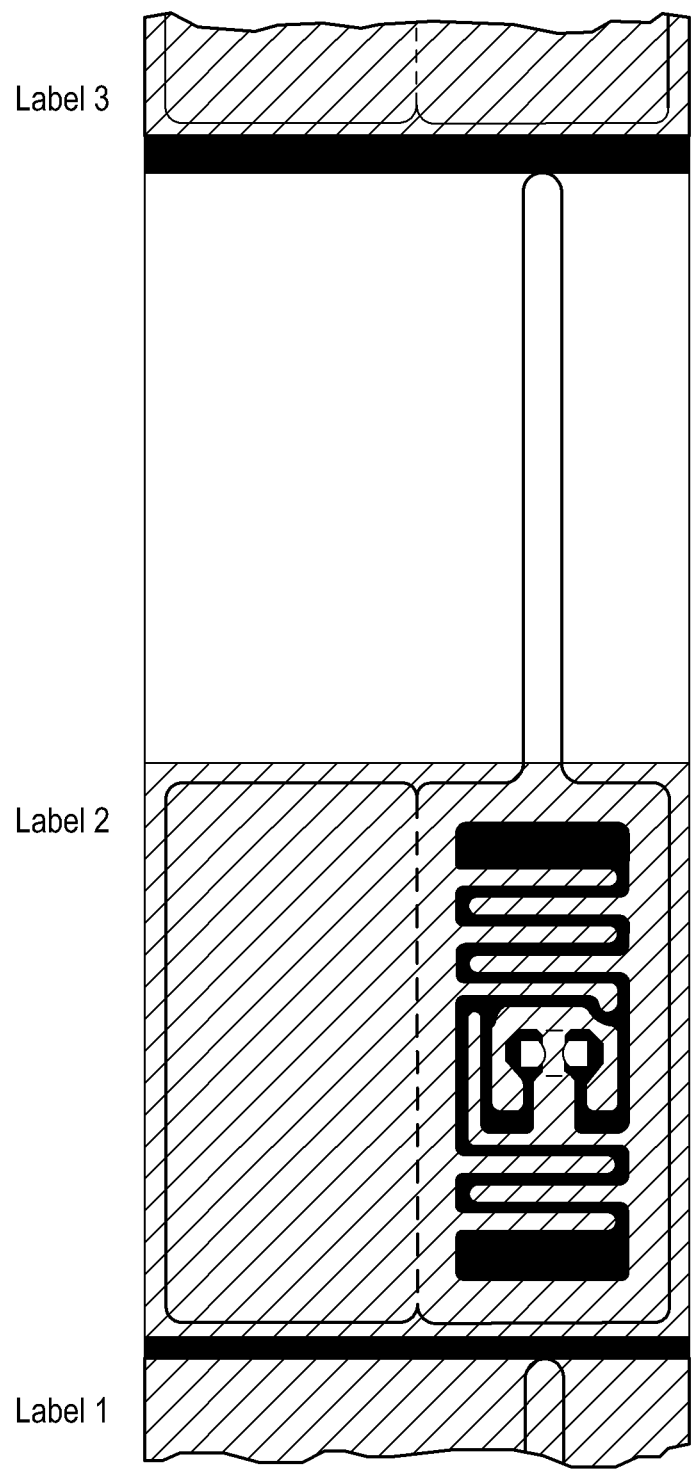

FIGS. 14A through 14D are diagrams of a label 1400 that can be used to attach an RFID tag to various items of a pharmacy kit according to an embodiment of the inventive concept. In particular, FIG. 14A shows label 1400 in a configuration prior to use, and FIG. 14B shows label 1400 in a configuration for attachment to a pharmaceutical item. FIG. 14C shows an example of label 1400 with example dimensions and an embedded RFID device 1435, and FIG. 14D shows label 1400 in the context of a printable roll.

Label 1400 is designed such that it can be securely attached to different types of items in a pharmacy kit without occluding labeling information. For example, label 1400 can be used in such a way that it hangs off the side of a vial, ampule, or other product where it may be inappropriate to place the main portion of the label directly on the product or product packaging. Alternatively, label 1400 can be attached to an item such that it does not hang off the side. A configuration where a portion of label 1400 hangs off the side of an item will be referred to as a "flagged" configuration.

Referring to FIG. 14A, label 1400 comprises a first portion 1405 having a printed portion 1410 and a flap portion 1415 separated by a perforation indicated by a dotted line. Label 1400 further comprises a second portion 1420 having a tail 1425 attached to first portion 1405, and a backing 1430 designed to be removed when tail 1425 is adhered to an item.

First and second portions 1405 and 1420 both have an adhesive backing. Accordingly, where label 1400 is used in the flagged configuration, adhesive backing portions of printed portion 1410 and flap portion 1415 may be folded together along the perforation to prevent them from sticking to other objects. Where label 1400 is not used in the flagged configuration (e.g., when it is attached to a boxed item), first and second portions 1405 and 1420 may both be adhered to an item. Moreover, where label 1400 is not used in the flagged configuration, flap portion 1415 may be removed by detaching it from printed portion 1410 along the perforation.

Printed portion 1410 and flap portion 1415 are typically formed with a substrate material comprising a common labeling material such as paper or plastic. Printed portion 1410 further comprises an embedded RFID device attached to the substrate. An example of such an RFID device is shown by RFID device 1435 in FIG. 14C. The substrate material can be printed with identifying information for an item. Among the printed information, there may be a bar code for backward compatibility, or human-readable information related to the item or label 1400. The RFID device can be encoded with identifying information through RFID printing.

The adhesive side of tail 1425 can be used to attach label 1400 to a kit item. Prior to use, the adhesive side is attached to backing 1430. Tail 1425 is typically formed of a transparent material to avoid obscuring information on the items in a kit. In general, when labeling medical items such as pharmaceuticals, it is important not to obscure labels, warnings, and other information on the packaging. The use of a transparent tail 1425 avoids this problem by allowing the user to see through any portion of the tail that may be attached to an item. Moreover, the shape of tail 1425 and allows an RFID tag to be attached to and/or hang off items having various different types of packaging. As examples, tail 1425 can be wrapped around a vial or ampule while allowing first portion 1405 to hang off. Similarly, it can be attached to a face of a box or a panel of a bag.

As alternatives to the example of FIG. 14A, the size of the tail may vary, and the perforated portion may be omitted. The tail size, for example, may be at least as large as the printable labeling portion.

Referring to FIG. 14B, label 1400 is shown in a configuration used to attach it to an item, which is illustrated conceptually by a dotted rectangle. When label 1400 is attached to the item, flap portion 1415 is adhered over printed portion 1410, and tail 1425 is adhered to the item while first portion 1405 hangs off of it.

Referring to FIG. 14C, label 1400 may have example dimensions as shown. However, these dimensions may vary in alternative embodiments. In addition, label 1400 may comprise RFID 1435 as shown, although other devices or device configurations can be used in alternative embodiments.

Referring to FIG. 14D, label 1400 is shown in the context of a roll comprising successive printable labels that can be fed into an RFID printer. In particular, label 1400 is shown as a second label among three successive labels "label 1", "label 2", and "label 3". These labels are separated from each other by a small gap having a vertical sense mark used for alignment with an RFID printer.

The foregoing is illustrative of embodiments and is not to be construed as limiting thereof. Although a few embodiments have been described, those skilled in the art will readily appreciate that many modifications are possible in the embodiments without materially departing from the novel teachings and advantages of the inventive concept. Accordingly, all such modifications are intended to be included within the scope of the inventive concept as defined in the claims.

What is claimed is:

1. A system for managing pharmacy kits, comprising:
   a reading station, comprising:
   a pharmacy kit container formed of a material designed to provide electromagnetic shielding,
   wherein each of the pharmacy kits is a transportable container having a collection of pharmacy items for a common purpose that can be deployed for a specific medical procedure, for a specific physician, or to a designated location, and
   wherein the pharmacy kit container is configured to temporarily enclose the pharmacy kit for verification, and
   an antenna coupled to the pharmacy kit container;
   computer-executable instructions that when executed by a processor cause the processor to:
   cause the antenna to emit a radio signal at least within the pharmacy kit container, and
   receive tag information from a plurality of radio frequency identification (RFID) tags coupled to a plurality of medicinal containers configured to store a plurality of drugs, the plurality of RFID tags being associated with a pharmacy kit located within the pharmacy kit container,
   wherein for the plurality of RFID tags, a particular RFID tag is coupled to a particular medicinal container of the plurality of medicinal containers and the particular medicinal container is configured to store a particular drug of the plurality of drugs, and
   wherein the particular RFID tag is associated with drug data of the particular drug, the drug data comprising at least an identifier of the particular drug and an expiration of the particular drug; and
   an information processing system communicatively coupled to the reading station and configured to:
   verify a first drug of the plurality of drugs using the tag information, wherein to verify the first drug, the information processing system is configured to:
   determine whether a first medicinal container associated with the first drug is present based at least in part on the tag information received from the plurality of RFID tags,
   based at least upon a determination that the first medicinal container is not present in the pharmacy kit, determine whether a second medicinal container configured to store a substitute first drug is present based at least in part on the tag information,
   based at least upon a determination that the second medicinal container is present, determine whether an expiration of the substitute first drug satisfies an expiration threshold based at least in part on the drug data associated with a first RFID tag of the plurality of RFID tags, wherein the first RFID tag is coupled to the second medicinal container, and
   based at least upon a determination that the expiration of the substitute first drug satisfies the expiration threshold, verify the first drug,
   identify any drugs that are missing from the pharmacy kit based at least in part on the tag information received from the plurality of RFID tags and a template for the pharmacy kit,
   identify any drugs of the plurality of drugs that do not satisfy the expiration threshold based at least in part on the tag information received from the plurality of RFID tags, and
   cause a display to display information regarding the plurality of drugs in the pharmacy kit including the substitute first drug, the any drugs that are missing from the pharmacy kit, and the any drugs of the plurality of drugs that do not satisfy the expiration threshold.

2. The system of claim 1, wherein to identify the any drugs that are missing from the pharmacy kit the information processing system is configured to compare the tag information with the template, wherein the template specifies a plurality of segments for the pharmacy kit and a quantity of pharmaceutical items including the plurality of medications from each segment to be included in the pharmacy kit.

3. The system of claim 1, wherein the information processing system is configured to monitor locations of a plurality of pharmacy kits based at least in part on information received from a real-time tracking system regarding the locations of the plurality of pharmacy kits.

4. The system of claim 1, wherein the template identifies the substitute first drug as an acceptable substitute for the first drug.

5. The system of claim 1, wherein the information processing system stores the template and kit records of the pharmacy kit.

6. The system of claim 1, wherein the pharmacy kit container is configured to receive only one pharmacy kit at a time.

7. The system of claim 1, wherein the information processing system stores a virtual history for each of the plurality of the pharmacy kit and updates the virtual history in response to a transaction involving the pharmacy kit.

8. A method of managing pharmacy kits, comprising:
receiving tag information of a plurality of radio frequency identification (RFID) tags coupled to a plurality of medicinal containers based at least in part on an antenna coupled to a pharmacy kit container emitting a radio signal at least within the pharmacy kit container,
wherein each of the pharmacy kits is a transportable container having a collection of pharmacy items for a common purpose that can be deployed for a specific medical procedure, for a specific physician, or to a designated location, and
wherein the pharmacy kit container is configured to temporarily enclose the pharmacy kit for verification,
wherein the pharmacy kit container provides electromagnetic shielding,
wherein the plurality of medicinal containers is configured to store a plurality of medications and the plurality of RFID tags is associated with the pharmacy kit located within the pharmacy kit container,
wherein for the plurality of RFID tags, a particular RFID tag is coupled to a particular medicinal container of the plurality of medicinal containers and the particular medicinal container is configured to store a particular medication of the plurality of medications, and
wherein the particular RFID tag is associated with medication data of the particular medication, the medication data comprising at least an identifier of the particular medication and an expiration of the particular medication;
verifying the plurality of medications within the pharmacy kit including at least a first medication of the plurality of medications using the tag information, wherein verifying the at least a first medication comprises:
determining that a first medicinal container associated with the first medication is not present in the pharmacy kit based at least in part on the tag information received from the plurality of RFID tags,
determining that a second medicinal container configured to store a substitute first medication is present in the pharmacy kit based at least in part on the tag information, and
determining that an expiration of the substitute first medication satisfies an expiration threshold based at least in part on the medication data associated with a first RFID tag of the plurality of RFID tags, wherein the first RFID tag is coupled to the second medicinal container; and
causing a display to display results of the verifying the plurality of medications including information regarding the substitute first medication.

9. The method of claim 8, further comprising identifying any missing medications in the pharmacy kit based at least in part on a comparison between the tag information and a template of the pharmacy kit.

10. The method of claim 9, further comprising generating a report indicating the any missing medications.

11. The method of claim 9, further comprising generating billing information for a medical patient based on the any missing medications.

12. The method of claim 9, further comprising determining at least one medication of the plurality of medications is expired based at least in part on an amount of time since the at least one medication was removed from refrigeration.

13. The method of claim 9, further comprising
determining any near expired medications of the plurality of medications based at least in part on a predetermined expiration margin; and
generating a report indicating the near expired medications.

14. A method of managing a pharmacy kit, comprising:
receiving tag information of a plurality of radio frequency identification (RFID) tags coupled to a plurality of pharmacy item containers located within the pharmacy kit, based at least in part on an antenna coupled to a pharmacy kit container emitting a radio signal at least within the pharmacy kit container that provides electromagnetic shielding and that is configured to temporarily enclose the pharmacy kit for verification,
wherein the pharmacy kit is a transportable container having a collection of pharmacy items for a common purpose that can be deployed for a specific medical procedure, for a specific physician, or to a designated location,
wherein the plurality of pharmacy item containers is configured to store a plurality of pharmacy items,
wherein a particular RFID tag of the plurality of RFID tags is coupled to a particular pharmacy item container of the plurality of pharmacy item containers and the particular pharmacy item container is configured to store a particular pharmacy item of the plurality of pharmacy items, and
wherein the particular RFID tag is associated with particular pharmacy item data comprising at least an identifier of the particular pharmacy item;
verifying the plurality of pharmacy items including at least a first pharmacy item of the plurality of pharmacy items within the pharmacy kit for deployment using the tag information, wherein verifying the at least a first pharmacy item comprises:
determining that a first pharmacy item container configured to store the first pharmacy item is not present in the pharmacy kit based at least in part on the tag information, and
determining that a second pharmacy item container configured to store a substitute first pharmacy item is present based at least in part on the tag information; and
causing a display to display results of the verifying the plurality of pharmacy items including information regarding the substitute first pharmacy item.

15. The method of claim 14, wherein the verifying the plurality of pharmacy items further comprises comparing pharmacy item data with a pharmacy kit template, wherein the pharmacy item data is associated with the tag information and comprises at least the particular pharmacy item data.

16. The method of claim 15, wherein the pharmacy kit template specifies a group of pharmacy items that form at least a portion of a pharmacy kit.

17. The method of claim 16, wherein the verifying the plurality of pharmacy items further comprises identifying one or more missing pharmacy items of the pharmacy kit based at least in part on comparing the pharmacy item data with the pharmacy kit template.

18. The method of claim 14, wherein the verifying the plurality of pharmacy items further comprises determining at least one pharmacy item of the plurality of pharmacy items is expired based at least in part on an amount of time since the at least one pharmacy item was removed from refrigeration.

19. The method of claim 14, wherein the verifying the plurality of pharmacy items further comprises determining at least one pharmacy item of the plurality of pharmacy items is expired based at least in part on a determination that the at least one pharmacy item does not satisfy an expiration threshold.

20. A system for managing a pharmacy kit, comprising:
one or more processors communicatively coupled to an antenna, the one or more processors configured to:
receive tag information of a plurality of RFID tags coupled to a plurality of pharmacy item containers based at least in part on the antenna emitting a radio signal at least within a pharmacy kit container that provides electromagnetic shielding and that is configured to temporarily enclose the pharmacy kit for verification, wherein the pharmacy kit is a transportable container having a collection of pharmacy items for a common purpose that can be deployed for a specific medical procedure, for a specific physician, or to a designated location,
wherein the plurality of pharmacy item containers is configured to store a plurality of pharmacy items,
wherein a particular RFID tag of the plurality of RFID tags is coupled to a particular pharmacy item container of the plurality of pharmacy item containers and the particular pharmacy item container is configured to store a particular pharmacy item of the plurality of pharmacy items, and
wherein the particular RFID tag is associated with particular pharmacy item data comprising at least an identifier of the particular pharmacy item;
verify the pharmacy kit for deployment using the tag information, wherein to verify the pharmacy kit, the one or more processors are configured to at least one of:
determine that a first pharmacy item container configured to store a first pharmacy item is not present based at least in part on the tag information, and determine that a second pharmacy item container configured to store a substitute first pharmacy item is present based at least in part on the tag information,
determine that the first pharmacy item is subject to a recall based at least in part on the tag information, or
identify the first pharmacy item as an expired pharmacy item based at least in part on a determination that an expiration of the first pharmacy item does not satisfy an expiration threshold; and
cause a display to display results of the verification of the pharmacy kit.

21. The system of claim 20, wherein to verify the plurality of pharmacy items, the one or more processors are further configured to compare pharmacy item data with a pharmacy kit template, wherein the pharmacy item data is associated with the tag information and comprises at least the particular pharmacy item data.

22. The system of claim 21, wherein the pharmacy kit template specifies a group of pharmacy items that form at least a portion of a pharmacy kit.

23. A method, comprising:
causing an antenna coupled to a pharmacy kit within a pharmacy kit container to emit a radio signal at least within the pharmacy kit container, the pharmacy kit container including an enclosed space for receiving a pharmacy kit and at least one door, wherein the enclosed space is accessible through the at least one door, and wherein the pharmacy kit is a transportable container having a collection of pharmacy items for a common purpose that can be deployed for a specific medical procedure, for a specific physician, or to a designated location;
receiving tag information associated with a plurality of radio frequency identification (RFID) tags located within the pharmacy kit container based at least in part on the antenna emitting the radio signal, the plurality of RFID tags being coupled to a plurality of pharmacy item containers,
wherein the pharmacy kit container is configured to temporarily enclose the pharmacy kit for verification and provides electromagnetic shielding,
wherein the plurality of pharmacy item containers is configured to store a plurality of pharmacy items,
wherein the plurality of pharmacy items constitutes the collection of pharmacy items of the pharmacy kit,
wherein a particular RFID tag of the plurality of RFID tags is coupled to a particular pharmacy item container of the plurality of pharmacy item containers and the particular pharmacy item container is configured to store a particular pharmacy item of the plurality of pharmacy items, and
wherein the particular RFID tag is associated with particular pharmacy item data comprising at least an identifier of the particular pharmacy item;
verifying the pharmacy kit based at least in part on the received tag information and a pharmacy kit template stored in a non-transitory computer-readable medium, wherein the pharmacy kit template identifies a group of pharmacy items that form at least a portion of the pharmacy kit, and wherein said verifying the pharmacy kit comprises comparing pharmacy item data associated with the plurality of RFID tags with the pharmacy kit template; and
causing a display to display results of verification of the pharmacy kit.

24. The method of claim 23, wherein the tag information associated with the plurality of RFID tags coupled to the plurality of pharmacy item containers is first tag information, the method further comprising:
receiving second tag information associated with an RFID tag associated with the pharmacy kit based at least in part on the antenna emitting the radio signal at least within the enclosed space of the pharmacy kit container;
determining a kit type based at least in part on the second tag information; and
identifying the pharmacy kit template from a plurality of pharmacy kit templates based at least in part on the determined kit type, wherein the pharmacy kit is verified based at least in part on the first tag information and the identified pharmacy kit template.

25. The method of claim 23, wherein verifying the pharmacy kit comprises determining that a first pharmacy item is not present and determine that a second pharmacy item container configured to store a substitute pharmacy item for the first pharmacy item is present based at least in part on said comparing the pharmacy item data associated with the plurality of RFID tags with the pharmacy kit template.

26. The method of claim 23, wherein verifying the pharmacy kit comprises identifying at least one missing pharmacy item not present in the pharmacy kit by said comparing the pharmacy item data associated with the plurality of RFID tags with the pharmacy kit template, wherein the pharmacy item data associated with the plurality of RFID tags is associated with the tag information and comprises at least the particular pharmacy item data.

27. The method of claim 23, wherein verifying the pharmacy kit comprises determining that a first pharmacy item is an extra item based at least in part on a determination that the first pharmacy item exceeds a threshold number of the group of pharmacy items identified by the pharmacy kit template.

28. The method of claim 23, wherein verifying the pharmacy kit comprises determining whether any of the plurality of pharmacy items are subject to a recall.

29. The method of claim 23, wherein verifying the pharmacy kit comprises determining whether an expiration of each of the plurality of pharmacy items satisfies an expiration threshold.

30. A system, comprising:
one or more processors; and
a non-transitory, computer-readable medium storing computer-executable instructions that when executed by the one or more processors, cause the one or more processors to at least:
cause an antenna coupled to a pharmacy kit container to emit a radio signal at least within the pharmacy kit container, the pharmacy kit container providing electromagnetic shielding;
receive tag information associated with a plurality of RFID tags coupled to a plurality of pharmacy item containers located within a pharmacy kit based at least in part on the antenna emitting the radio signal at least within the pharmacy kit container, wherein the pharmacy kit is a transportable container having a collection of pharmacy items for a common purpose that can be deployed for a specific medical procedure, for a specific physician, or to a designated location
wherein a particular RFID tag of the plurality of RFID tags is coupled to a particular pharmacy item container of the plurality of pharmacy item containers and the particular pharmacy item container is configured to store a particular pharmacy item;
verify the pharmacy kit based at least in part on the received tag information, wherein to verify the pharmacy kit, the computer-executable instructions when executed cause the one or more processors to at least one of:
determine that a first RFID tag associated with a first pharmacy item container configured to store a first pharmacy item is not present, and determine that a third RFID tag associated with a substitute pharmacy item container configured to store a substitute pharmacy item is present,
determine that a second pharmacy item associated with a second RFID tag of the plurality of RFID tags is subject to a recall, or identify the second pharmacy item associated with the second RFID tag as an expired pharmacy item based at least in part on a determination that an expiration of the second pharmacy item does not satisfy an expiration threshold; and
cause a display to display results of verification of the pharmacy kit.

31. The system of claim 30, wherein the tag information associated with the plurality of RFID tags coupled to the plurality of pharmacy item containers is first tag information, and wherein the computer-executable instructions further cause the one or more processors to:
receive second tag information associated with an RFID tag associated with the pharmacy kit based at least in part on the antenna emitting the radio signal at least within the pharmacy kit container;
determine a kit type based at least in part on the second tag information;
identify a pharmacy kit template from a plurality of pharmacy kit templates based at least in part on the determined kit type; and
verify the pharmacy kit based at least in part on the first tag information and the identified pharmacy kit template, wherein the pharmacy kit template identifies a group of pharmacy items that form at least a portion of the pharmacy kit.

32. The system of claim 31, wherein to verify the pharmacy kit based at least in part on the first tag information and the pharmacy kit template, the computer-executable instructions when executed cause the one or more processors to compare at least a portion of the first tag information with the pharmacy kit template.

33. The system of claim 31, wherein to verify the pharmacy kit based at least in part on the first tag information and the pharmacy kit template, the computer-executable instructions when executed cause the one or more processors to compare pharmacy item data with the pharmacy kit template, wherein the pharmacy item data is associated with the first tag information.

34. The system of claim 33, wherein the pharmacy item data is stored in a non-transitory computer-readable medium apart from the plurality of RFID tags and the tag information is used to access the pharmacy item data.

35. The system of claim 31, wherein to verify the pharmacy kit, the computer-executable instructions when executed cause the one or more processors to determine that the first RFID tag associated with the first pharmacy item container configured to store the first pharmacy item is not present, and determine that the third RFID tag associated with the substitute pharmacy item container configured to store the substitute pharmacy item is present.

36. The system of claim 31, wherein to verify the pharmacy kit, the computer-executable instructions when executed cause the one or more processors to determine that the second pharmacy item is subject to the recall.

37. The system of claim 31, wherein to verify the pharmacy kit, the computer-executable instructions when executed cause the one or more processors to identify the second pharmacy item as an expired pharmacy item based at least in part on the determination that the expiration of the second pharmacy item does not satisfy the expiration threshold.

* * * * *